United States Patent
Soni et al.

(10) Patent No.: US 9,944,660 B2
(45) Date of Patent: Apr. 17, 2018

(54) TRICYCLIC BENZOXABOROLES AS ANTIBACTERIAL AGENTS

(71) Applicant: Daiichi Sankyo Company, Limited, Chuo-ku, Tokyo (JP)

(72) Inventors: Ajay Soni, Gurgaon (IN); Aditi Agarwal, Gurgaon (IN); Sangram Shesharao Deshmukh, Gurgaon (IN); Kedar Padmakar Purnapatre, Gurgaon (IN); Shinji Marumoto, Shinagawa-ku (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/393,996

(22) Filed: Dec. 29, 2016

(65) Prior Publication Data

US 2017/0174709 A1    Jun. 22, 2017

Related U.S. Application Data

(63) Continuation of application No. PCT/IB2015/054903, filed on Jun. 30, 2015.

(30) Foreign Application Priority Data

Jul. 1, 2014    (IN) .......................... 1777/DEL/2014

(51) Int. Cl.
   *C07F 5/02*    (2006.01)

(52) U.S. Cl.
   CPC .................................. *C07F 5/025* (2013.01)

(58) Field of Classification Search
   CPC ....................................................... C07F 5/025
   See application file for complete search history.

(56) References Cited

U.S. PATENT DOCUMENTS

| 8,039,450 B2 * | 10/2011 | Akama | A61K 31/69 514/64 |
| 8,461,135 B2 * | 6/2013 | Akama | A61K 31/69 514/64 |

FOREIGN PATENT DOCUMENTS

| WO | 2006/089067 A2 | 8/2006 |
| WO | 2012/033858 A2 | 3/2012 |

OTHER PUBLICATIONS

O'Dwyer, K., et al., "Bacterial Resistance to Leucyl-tRNA Synthetase Inhibitor GSK2251052 Develops During Treatment of Complicated Urinary Tract Infections," Antimicrobial Agents and Chemotherapy 59(1):289-298, Jan. 2015.
Sievert, D.M., et al., "Antimicrobial-Resistant Pathogens Associated With Healthcare-Associated Infections: Summary of Data Reported to the National Healthcare Safety Network at the Centers for Disease Control and Prevention, 2009-2010," IInfection Control and Hospital Epidemiology 34(1):1-14, Jan. 2013.
Zane, L.T., et al., "Safety, Tolerability, and Pharmacokinetics of a Novel Gram-Negative Antimicrobial, GSK2251052, in Healthy Subjects," Proceedings of the 21st ECCMID, May 7-10, 2011, Milan, Italy, Poster Session P1521, 1 page.

(Continued)

*Primary Examiner* — Golam M Shameem
(74) *Attorney, Agent, or Firm* — Christensen O'Connor Johnson Kindness PLLC

(57) ABSTRACT

The present invention provides a tricyclic compound represented by general formula (I), a pharmaceutical salt thereof, or a stereoisomer thereof exhibits excellent antibacterial activity against Gram-negative bacteria resistant bacteria thereof, and also being excellent in terms of safety. Furthermore, the present invention provides production processes, pharmaceutical compositions comprising a tricyclic compound, a pharmaceutically acceptable salt thereof, or a stereoisomer thereof as an active ingredient and use thereof as a pharmaceutical agent. The compounds of the present invention are useful for the treatment and/or prevention of disease such as complicated urinary tract infections (cUTIs), nosocomial pneumonia, intra-abdominal infections (IAIs) or bacteremia.

formula (I)

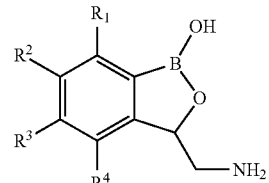

formula (Ia)

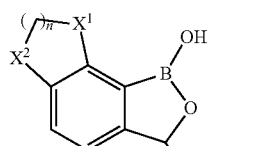

formula (Ib)

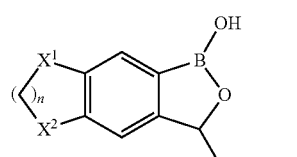

formula (Ic)

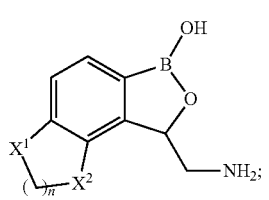

8 Claims, No Drawings

(56) References Cited

OTHER PUBLICATIONS

Zilberberg, M.D., and A.F. Shorr, "Secular Trends in Gram-Negative Resistance Among Urinary Tract Infection—Hospitalizations in the United States, 2000-2009," Infection Control and Hospital Epidemiology 34(9):940-946, Sep. 2013.
International Search Report and Written Opinion dated Oct. 5, 2015, issued in corresponding International Application PCT/IB2015/054903, filed Jun. 30, 2015, 10 pages.
International Preliminary Report on Patentability dated Jan. 3, 2017, issued in corresponding International Application PCT/IB2015/054903, filed Jun. 30, 2015, 7 pages.
First Office Action dated Oct. 20, 2017, issued in Chinese Application No. 2015800359197, filed Jun. 30, 2015, 11 pages.

* cited by examiner

TRICYCLIC BENZOXABOROLES AS ANTIBACTERIAL AGENTS

FIELD OF THE INVENTION

The present invention provides a tricyclic compound a stereoisomer, or a pharmaceutically acceptable salt thereof, having excellent antibacterial activity against Gram-negative bacteria and also being excellent in terms of safety. Furthermore, the present invention provides a pharmaceutical compositions comprising a tricyclic compound, a stereoisomer, or a pharmaceutically acceptable salt thereof as a pharmaceutically active ingredient. Particularly, the present invention provides tricyclic compounds, a stereoisomer, or a pharmaceutically acceptable salts thereof useful for the treatment and/or prevention of infectious diseases caused by Gram-negative bacteria or resistant bacteria thereof.

BACKGROUND OF THE INVENTION

There has been a worldwide increase in the number of infections caused by Gram-negative bacteria. The resistant Gram-negative bacteria has been a serious global health concern as is evident from U.S. Centers for Disease Control and Prevention (CDC) report on Antibiotic Resistant Threats in the United States, 2013.

Gram-negative bacteria are common causes of intra-abdominal infections (IAIs), urinary tract infections (UTIs), nosocomial pneumonia, and bacteremia. *Escherichia coli, Klebsiella pneumoniae* and *Pseudomonas aeruginosa* are important pathogens accounting for 27% of all pathogens and 70% of all Gram-negative pathogens causing healthcare-associated infections (Sievert D M, et al., *Infect Control Hosp Epidemiol.* 2013; 34:1-14). *P. aeruginosa* is the most common Gram-negative cause of nosocomial pneumonia and the second most common cause of catheter-related UTIs and *E. coli* is the most common cause of UTIs (Sievert D M, et al., *Infect Control Hosp Epidemiol*, 2013; 34:1-14). Cases of UTI caused by extended spectrum beta lactamase (ESBL)-producing *E. coli* and *K. pneumonia* as well as *P. aeruginosa*, including multidrug-resistant (MDR) strains are increasing (Zilberberg M D, et al., *Infect Control Hosp Epidemiol.* 2013; 34:940-946).

Treatment options for infections caused by Gram-negative bacteria and resistant bacteria thereof are very limited. Therefore, there is a serious need for a new antibiotic having a novel mechanism of action to meet the needs of the patients.

As such benzoxaborole compounds have been known which inhibit leucyl-tRNA synthetase (LRS enzyme), for example WO 2012/33858, WO 2011/60199, WO 2011/49971, WO 2011/037731, WO 2010/080558, WO 2009/140309, WO 2008/157726 and WO 2008/70257. The PCT publication WO 2013/154759 provides a combination of an amino acid or amino acid salt that is capable of being acylated onto tRNA$^{leu}$ by LRS and a benzoxaborole compound.

Other references disclosing benzoxaborole as a structural moiety includes WO2014/173880, WO2014/149793, WO2014/121124, WO2014/07831, WO2013/78070, WO 2011/094450, WO 2011/063293, WO 2011/022337, WO 2011/019616, WO 2011/019612, WO 2011/19618, WO 2011017125, WO 2010/45503, WO 2010/45505, WO 2010/027975, WO 2010/028005, WO 2009/111676, WO 2007/146965, WO 2007/131072, WO 2007/095638, WO 2007/78340, WO 2006/089067 and WO 2005/013892.

However, none of the cited references disclose tricyclic benzoxaborole compounds, provided in the present invention, as antibacterial agents targeting Gram-negative bacteria and resistant bacteria thereof for the treatment and/or prevention of bacterial infections, for example intra-abdominal infections (IAIs), complicated urinary tract infections (cUTIs), nosocomial pneumonia or bacteremia.

WO2015/21396, WO2015/16558 and WO2013/93615 disclose tricyclic boron compounds. None of the aforementioned specifically contemplates any compound provided in the present invention.

GSK2251052 (benzoxaborole compound) is the first antibacterial investigational drug of this class, as reported, for example, by Zane et al., in a poster Safety, tolerability, and pharmacokinetics of a novel Gram-negative antimicrobial, in healthy subjects, 21$^{st}$ European Congress of Clinical Microbiology and Infectious Diseases, 2011, Milan, Italy. The clinical development of GSK2251052 (or AN3365) has been discontinued due to the identification of microbiological findings of resistance in the Phase 2b trial for the treatment of complicated urinary tract infections (O'Dwyer K, et. al *Antimicrob Agents Chemother.* 2015; 59(1):289-98). It has been considered that such benzoxaborole compounds are not suitable for applying to clinical settings.

However, compounds of the present invention have been found to be suitable for applying in clinical settings. They have much improved profile over AN3365, for example 1) in terms of resistance on treatment, 2) no significant shift in MICs in *Pseudomonas* efflux deleted and over-expression strains, 3) retains activity in human urine, 4) lacks putative site of metabolism and is stable in human S9. *Pseudomonas* has strong efflux mechanism that is responsible for resistance to existing drugs. Compounds of the present invention works on such efflux over-expressing clinical isolates. In addition, compounds of the present invention were found to be safe and efficacious.

Thus, the present invention provides a great hope for a new antibiotic to meet the challenges of a serious global health concern due to Gram-negative bacteria and resistant bacteria thereof causing bacterial infections including, but not limited to, intra-abdominal infections (IAIs), complicated urinary tract infections (cUTIs) or nosocomial pneumonia.

SUMMARY OF THE INVENTION

The Problem to be Solved by the Invention

There is a need for the development of a new antibiotic, which exhibits strong antibacterial activity against Gram-negative bacteria and the resistant bacteria thereof, and at the same time possess excellent solubility and safety profile amenable to human use.

The Means to Solve the Problem

As a result of intensive studies, the present inventors have found that a compound represented by general formula (I), a stereoisomer, or a pharmaceutically acceptable salt thereof exhibits strong antibacterial activity against Gram-negative bacteria and the resistant bacteria thereof, and also has excellent solubility and safety. In particular, the compounds of the present invention have excellent antibacterial activity and are therefore useful for treating and/or preventing bacterial infectious disease caused by Gram-negative bacteria and resistant bacteria thereof. For instance, the compounds of the present invention are useful for treating and/or preventing a disease such as complicated urinary tract infections (cUTIs), nosocomial pneumonia, intra-abdominal infections (IAIs) or bacteremia.

Thus, in one aspect, the present invention relates to:

[1] A compound represented by general formula (I), a stereoisomer, or a pharmaceutically acceptable salt thereof:

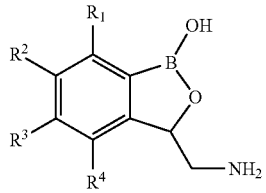

formula (I)

wherein, the adjacent two of $R^1$, $R^2$, $R^3$ and $R^4$ taken together with benzoxaborole structural moiety form tricyclic structure represented by the following formulae:

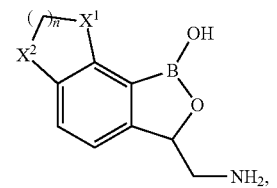

formula (Ia)

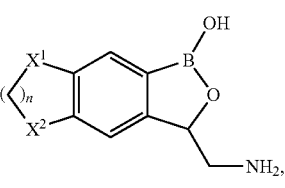

formula (Ib)

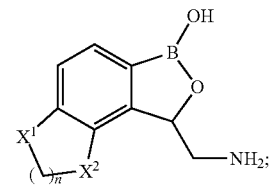

formula (Ic)

while the rest of the two of $R^1$, $R^2$, $R^3$ and $R^4$ which do not precipitate in tricyclic structure formation represent hydrogen atom, $X^1$ and $X^2$, each independently represents a methylene group or oxygen atom and n represents integer of 1 or 2.

The present invention may further relates to the following:

[2] The compound, a stereoisomer, or a pharmaceutically acceptable salt thereof according to [1], wherein the compound of the general formula (I) has the following structure:

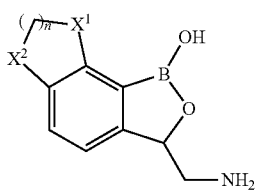

formula (Ia)

[3] The compound or a pharmaceutically acceptable salt thereof according to [1], wherein the compound of the general formula (I) has the following structure:

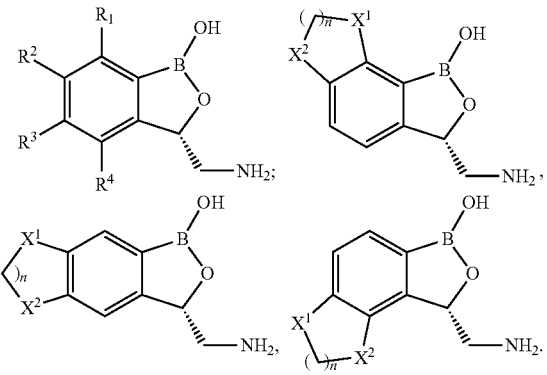

[4] The compound or a pharmaceutically acceptable salt thereof according to [1] or [3], wherein the compound of the general formula (I) has the following structure:

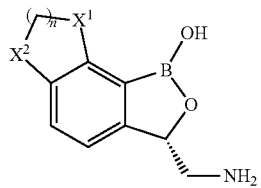

[5] The compound, a stereoisomer, or a pharmaceutically acceptable salt thereof according to any one of [1] to [4], wherein $X^1$ and $X^2$ represent oxygen atoms and n represents 1 or 2.

[6] The compound, a stereoisomer, or a pharmaceutically acceptable salt thereof according to any one of [1] to [4], wherein one of $X^1$ and $X^2$ represents oxygen and the other represents a methylene group, and n represents 1 or 2.

[7] The compound, a stereoisomer, or a pharmaceutically acceptable salt thereof according to any one of [1] to [4], wherein $X^1$ and $X^2$ represent methylene group and n represents 1 or 2.

[8] The compound, a stereoisomer, or a pharmaceutically acceptable salt thereof according to any one of [1] to [7], wherein the compound is selected from the group of:

3-(Aminomethyl)[1,3]dioxolo[4,5-f][2,1]benzoxaborol-1(3H)-ol hydrochloride, 3-(Aminomethyl)-6,7-dihydro[1,2]oxaborolo[3,4-g][1,4]benzodioxin-1(3H)-ol hydrochloride, 3-(Aminomethyl)-3,6,7,8-tetrahydro-1H-indeno[4,5-c][1,2]oxaborol-1-ol hydrochloride, 3-(Aminomethyl)-6,7,8,9-tetrahydronaphtho[1,2-c][1,2]oxaborol-1(3H)-ol hydrochloride, 8-(Aminomethyl)[1, 3]dioxolo[4,5-e][2,1]benzoxaborol-6(8H)-ol hydrochloride, (8S)-8-(Aminomethyl)[1,3]dioxolo[4,5-e][2,1]benzoxaborol-6(8H)-ol hydrochloride, 9-(Aminomethyl)-2,3-dihydro[1,2]oxaborolo[4,3-f][1,4]benzodioxin-7(9H)-ol hydrochloride, 3-(Aminomethyl)-7,8-dihydro[1,2]oxaborolo[3,4-f][1,4]benzodioxin-1(3H)-ol hydrochloride, 3-(Aminomethyl)[1]dioxolo[4,5-g][2,1]benzoxaborol-1(3H)-ol hydrochloride,
(3S)-3-(Aminomethyl)[1,3]dioxolo[4,5-g][2,1]benzoxaborol-1(3H)-ol hydrochloride,
3-(Aminomethyl)-5,6-dihydrofuro[3,2-f][2,1]benzoxaborol-1(3H)-ol hydrochloride, and
3-(Aminomethyl)-6,7-dihydrofuro[2,3-f][2,1]benzoxaborol-1 (3H)-ol hydrochloride.

[9] The compound or a pharmaceutically acceptable salt thereof according to [3] or [4], wherein the compound is (8S)-8-(Aminomethyl)[1,3]dioxolo[4,5-e][2,1]benzoxaborol-6(8H)-ol hydrochloride, or
(3S)-3-(Aminomethyl)[1,3]dioxolo[4,5-g][2,1]benzoxaborol-1(3H)-ol hydrochloride.

[10] A pharmaceutical composition comprising a therapeutically effective amount of a compound, a stereoisomer, or a pharmaceutically acceptable salt thereof according to any one of [1] to [9] as its active ingredient.

[11] A pharmaceutical composition according to [10], wherein said pharmaceutical composition is administered to treat or prevent bacterial infectious disease.

[12] The pharmaceutical composition according to [11], wherein said bacterial infectious disease one or more than one selected from complicated and uncomplicated urinary tract infection, hospital-acquired pneumonia, osteomyelitis, syphilis, intra-abdominal infections, nosocomial pneumonia, bacteremia, gynecological infection, respiratory tract infection, acute exacerbation of chronic bronchitis, cystic fibrosis, acute otitis media, acute sinusitis, catheter-related sepsis, *chlamydia*, community-acquired *pneumoniae*, endocarditis, febrile neutropenia, meningitis, gonococcal cervicitis, gonococcal urethritis, cystitis and pyelonephritis.

[13] The pharmaceutical composition according to [11], wherein said bacterial infectious disease is selected from intra-abdominal infections (IAIs), complicated urinary tract infections (cUTIs), nosocomial pneumonia or bacteremia.

[14] The pharmaceutical composition according to [11], wherein said bacterial infectious disease is that caused by Gram-negative bacteria or resistant bacteria thereof.

[15] The pharmaceutical composition according to [14], wherein said Gram-negative bacteria or resistant bacteria thereof is one or more than one bacteria selected from *Acinetobacter baumannii, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter coli, Campylobacter fetus, Citrobacter freundii, Citrobacter koseri, Edwarsiella tarda, Eikenella corroders, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydophila pneumoniae, Chlamydophila trachomatis, Ricketsia prowazekii, Coxiella burnetii, Ehrlichia chafeensis* or *Bartonella hensenae*. In a preferred embodiment of the present invention, the Gram-negative bacteria is selected from *Acinetobacter baumannii, Escherichia coli, Klebsiella pneumoniae* and *Pseudomonas aeruginosa*.

[16] The pharmaceutical composition according to [14], wherein said Gram-negative bacteria or resistant bacteria thereof is selected from *Escherichia coli, Klebsiella pneumoniae* or *Pseudomonas aeruginosa*.

[17] The pharmaceutical composition according to [14], wherein said Gram-negative bacteria or resistant bacteria thereof is selected from *Escherichia coli* or *Pseudomonas aeruginosa*.

[18] A compound, a stereoisomer, or a pharmaceutically acceptable salt thereof according to any one of [1] to [9] for use in treating bacterial infectious disease.

[19] The use according to [18], wherein said bacterial infectious disease is one or more than one selected from complicated and uncomplicated urinary tract infection, hospital-acquired pneumonia, osteomyelitis, syphilis, intra-abdominal infections, nosocomial pneumonia, bacteremia, gynecological infection, respiratory tract infection, acute exacerbation of chronic bronchitis, cystic fibrosis, acute otitis media, acute sinusitis, catheter-related sepsis, *chlamydia*, community-acquired *pneumoniae*, endocarditis, febrile neutropenia, meningitis, gonococcal cervicitis, gonococcal urethritis, cystitis and pyelonephritis.

[20] The use according to [18], wherein said bacterial infectious disease is selected from intra-abdominal infections (IAIs), complicated urinary tract infections (cUTIs), nosocomial pneumonia or bacteremia.

[21] The use according to [18], wherein said bacterial infectious disease is that caused by Gram-negative bacteria or resistant bacteria thereof.

[22] The use according to [21], wherein said Gram-negative bacteria or resistant bacteria thereof is one or more than one bacteria selected from *Acinetobacter baumannii, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis; Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter coli, Campylobacter fetus, Citrobacter freundii, Citrobacter koseri, Edwarsiella tarda, Eikenella corroders, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella mu/tocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moni/iformis, Vibrio cholerae, Vibrio parahaemolyticus, Vibrio vul-* nificus, *Vibrio alginolyticus, Yersinia enterocolitica, Yersinia pestis, Yersinia pseudotuberculosis, Chlamydophila pneumoniae, Chlamydophila trachomatis, Ricketsia prowazekii, Coxiella burnetii, Ehrlichia chafeensis* or *Bartonella hensenae*. In a preferred embodiment of the present invention, the Gram-negative bacteria is selected from *Acinetobacter baumannii, Escherichia coli, Klebsiella pneumoniae* and *Pseudomonas aeruginosa*.

[23] The use according to [21], wherein said Gram-negative bacteria or resistant bacteria thereof is selected from *Escherichia coli, Klebsiella pneumoniae* or *Pseudomonas aeruginosa*.

[24] The pharmaceutical composition according to [21], wherein said Gram-negative bacteria or resistant bacteria thereof is selected from *Escherichia coli* or *Pseudomonas aeruginosa*.

[25] A method for treating bacterial infectious disease in a patient comprising administering to said patient a therapeutically effective amount of a compound, a stereoisomer, or a pharmaceutical salt thereof according to any one of [1] to [9].

[26] The method of [25], wherein the bacterial infectious disease is one or more than one selected from complicated and uncomplicated urinary tract infection, hospital-acquired pneumonia, osteomyelitis, syphilis, intra-abdominal infections, nosocomial pneumonia, bacteremia, gynecological infection, respiratory tract infection, acute exacerbation of chronic bronchitis, cystic fibrosis, acute otitis media, acute sinusitis, catheter-related sepsis, *chlamydia*, community-acquired *pneumoniae*, endocarditis, febrile neutropenia, meningitis, gonococcal cervicitis, gonococcal urethritis, cystitis and pyelonephritis.

[27] The method according to [25], wherein bacterial infectious disease is selected from intra-abdominal infections (IAIs), complicated urinary tract infections (cUTIs), nosocomial pneumonia or bacteremia.

[28] The method of [25], wherein the infectious disease is that caused by Gram-negative bacteria or resistant bacteria thereof.

[29] The method of [28], wherein the Gram-negative bacteria or resistant bacteria thereof is selected from *Acinetobacter baumannii, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter coli, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyl, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydophila pneumoniae, Chiamydophila trachomatis, Ricketsia prowazekii, Coxiella bumetii, Ehrlichia chafeensis* or *Bartonella hensenae*. In a preferred embodiment of the present invention, the Gram-negative bacteria is selected from *Acinetobacter baumannii, Escherichia coli, Klebsiella pneumoniae* and *Pseudomonas aeruginosa*.

[30] The method according to [28], wherein Gram-negative bacteria is selected from *Escherichia coli, Klebsiella pneumoniae* or *Pseudomonas aeruginosa*.

[31] The method according to [28], wherein Gram-negative bacteria is selected from *Escherichia coli* or *Pseudomonas aeruginosa*.

[32] A leucyl-tRNA synthetase inhibitor for use in the treatment of bacterial infectious disease having the structure of formula (I), a stereoisomer, or a pharmaceutically acceptable salt thereof:

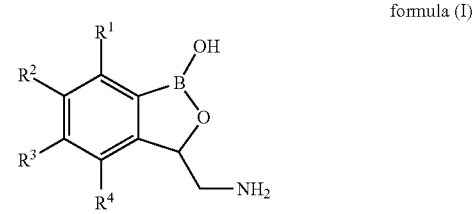

formula (I)

wherein, the adjacent two of $R^1$, $R^2$, $R^3$ and $R^4$ taken together with benzoxaborole structural moiety form tricyclic structure represented by the following formulae:

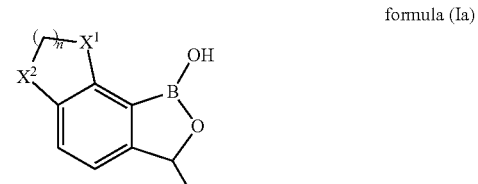

formula (Ia)

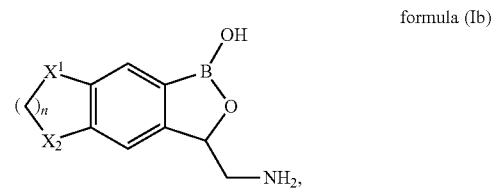

formula (Ib)

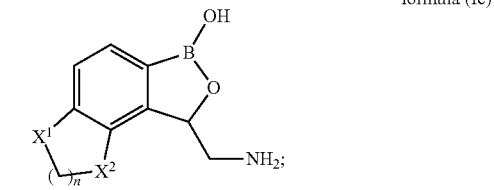

formula (Ic)

while the rest of the two of $R^1$, $R^2$, $R^3$ and $R^4$ which do not precipitate in tricyclic structure formation represent hydrogen atom, $X^1$ and $X^2$, each independently represents a methylene group or oxygen atom and n represents integer of 1 or 2.

[33] The leucyl-tRNA synthetase inhibitor according to [32], wherein the compound of the formula (I) has the following structure:

formula (Ia)

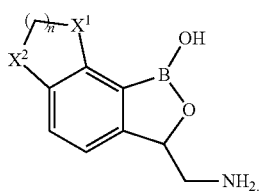

[34] The leucyl-tRNA synthetase inhibitor according to [32], wherein the compound of the formula (I) has the following structure:

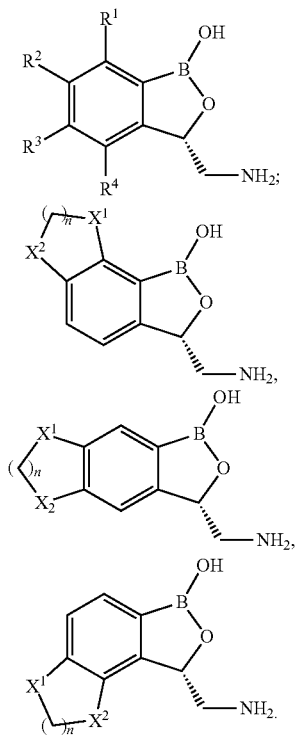

[35] The leucyl-tRNA synthetase inhibitor according to [34], wherein the compound of the formula (I) has the following structure:

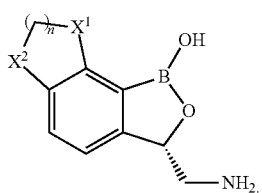

[35] The leucyl-tRNA synthetase inhibitor according to any one of [32] to [34], wherein the infectious disease is those caused by gram-negative bacteria or resistant bacteria thereof.

[36] The leucyl-tRNA synthetase inhibitor according to any one of [32] to [34], wherein the infectious disease is one or more than one selected from complicated and uncomplicated urinary tract infection, hospital-acquired pneumonia, osteomyelitis, syphilis, intra-abdominal infections, nosocomial pneumonia, bacteremia, gynecological infection, respiratory tract infection, acute exacerbation of chronic bronchitis, cystic fibrosis, acute otitis media, acute sinusitis, catheter-related sepsis, *chlamydia*, community-acquired *pneumoniae*, endocarditis, febrile neutropenia, meningitis, gonococcal cervicitis, gonococcal urethritis, cystitis and pyelonephritis.

[37] The leucyl-tRNA synthetase inhibitor according to [36], wherein said bacterial infectious disease is selected from intra-abdominal infections (IAIs), complicated urinary tract infections (cUTIs), nosocomial pneumonia or bacteremia.

[38] The leucyl-tRNA synthetase inhibitor according to any one of [32] to [34], wherein said bacterial infectious disease is that caused by Gram-negative bacteria or resistant bacteria thereof.

[39] The leucyl-tRNA synthetase inhibitor according to [38], wherein said Gram-negative bacteria or resistant bacteria thereof is one or more than one bacteria selected from *Acinetobacter baumannii, Acinetobacter haemolyticus, Actinobacillus actinomycetemcomitans, Aeromonas hydrophile, Bacteroides fragilis, Bacteroides theataioatamicron, Bacteroides distasonis, Bacteroides ovatus, Bacteroides vulgates, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter coli, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penned, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydophila pneumoniae, Chlamydophila trachomatis, Ricketsia prowazekii, Coxiella burnetii, Ehrlichia chafeensis or Bartonella hensenae.* In a preferred embodiment of the present invention, the Gram-negative bacteria is selected from *Acinetobacter baumannii, Escherichia coli, Klebsiella pneumoniae* and *Pseudomonas aeruginosa.*

[40] The leucyl-tRNA synthetase inhibitor according to [39], wherein said Gram-negative bacteria or resistant bacteria thereof is selected from *Escherichia Klebsiella pneumoniae* or *Pseudomonas aeruginosa.*

[41] The leucyl-tRNA synthetase inhibitor according to [39], wherein said Gram-negative bacteria or resistant bacteria thereof is selected from *Escherichia coli* or *Pseudomonas aeruginosa.*

[42] Use of the compound, a stereoisomer, or a pharmaceutically acceptable salt thereof according to any one of [1] to [9] for production of a therapeutic agent for bacterial infections.

[43] The use according to [42], wherein said bacterial infectious disease is one or more than one selected from complicated and uncomplicated urinary tract infection, hospital-acquired pneumonia, osteomyelitis, syphilis, intra-abdominal infections, nosocomial pneumonia, bacteremia, gynecological infection, respiratory tract infection, acute exacerbation of chronic bronchitis, cystic fibrosis, acute otitis media, acute sinusitis, catheter-related sepsis, *chlamydia*, community-acquired *pneumoniae*, endocarditis, febrile neutropenia, meningitis, gonococcal cervicitis, gonococcal urethritis, cystitis and pyelonephritis.

[44] The use according to [42], wherein said bacterial infectious disease is selected from intra-abdominal infections (IAIs), complicated urinary tract infections (cUTIs), nosocomial pneumonia or bacteremia.

[45] The use according to [42], wherein said bacterial infectious disease is that caused by Gram-negative bacteria or resistant bacteria thereof.

[46] The use according to [45], wherein said Gram-negative bacteria or resistant bacteria thereof is one or more than one bacteria selected from *Acinetobacter baumannii, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter coli, Campylobacter fetus, Citrobacter freundii, Citrobacter koseri, Edwarsiella tarda, Eikenella corroders, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydophila pneumoniae, Chlamydophila trachomatis, Ricketsia prowazekii, Coxiella burnetii, Ehrlichia chafeensis* or *Bartonella hensenae*. In a preferred embodiment of the present invention, the Gram-negative bacteria is selected from *Acinetobacter baumannii, Escherichia coli, Klebsiella pneumoniae* and *Pseudomonas aeruginosa*.

[47] The use according to [45], wherein said Gram-negative bacteria or resistant bacteria thereof is selected from *Escherichia coli, Klebsiella pneumoniae* or *Pseudomonas aeruginosa*,

[48] The pharmaceutical composition according to [45], wherein said Gram-negative bacteria or resistant bacteria thereof is selected from *Escherichia coli* or *Pseudomonas aeruginosa*.

The aforementioned aspects and embodiments, and other aspects, objects, features and advantages of the present invention will be apparent from the following detailed description and the appended claims thereof.

DETAILED DESCRIPTION OF THE INVENTION

As used herein the following definitions apply unless clearly indicated otherwise.

It should be understood that unless expressly stated to the contrary, "a compound of general formula (I)" refers to and includes any and all compounds described by formula (I), its embodiments, as well as subgenuses, inclusive of all salts, stereoisomers thereof. It should also be noted that the singular forms "a" "an" and "the" include plural reference unless the context clearly dictates otherwise.

In one aspect of the present invention, there is provided a compound of general formula (I), a stereoisomer, or a pharmaceutically acceptable salt thereof

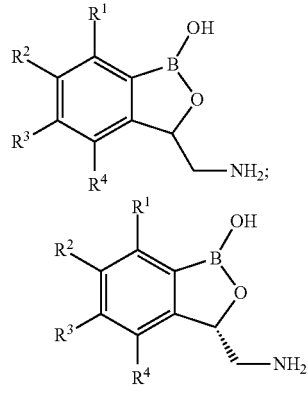

formula (I)

wherein the descriptors have the meaning as indicated above.

The compound of the present invention is characterized in that this has a tricyclic structure. This tricyclic structure is formed by adjacent two of $R^1$, $R^2$, $R^3$ and $R^4$ and with benzoxaborole structural moiety. This "adjacent two" is exemplified by the combination such as W and $R^2$, $R^2$ and $R^3$, or $R^3$ and $R^4$. The rest of the two which do not participate in the formation of the tricliclic structure represent hydrogen atom. For example, when $R^1$ and $R^2$ are selected to form tricyclic structure, then, $R^3$ and $R^4$ represent hydrogen atoms. The present invention includes following embodiments:

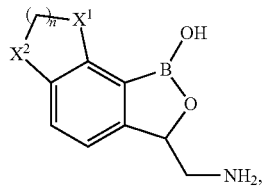

formula (Ia)

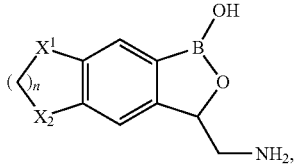

formula (Ib)

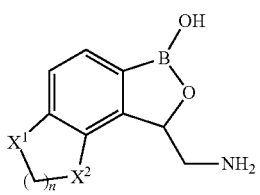

formula (Ic)

In a preferred embodiment, a compound of formula (Ia), a stereoisomer thereof, or a pharmaceutically acceptable salt thereof is provided;

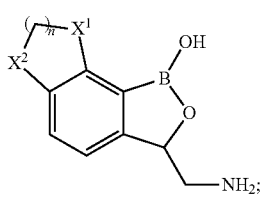

formula (Ia)

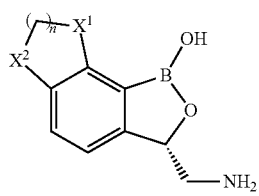

wherein $X^1$ and $X^2$, each independently represents a methylene group or oxygen atom and n represents 1 or 2.

In another preferred embodiment, a compound of formula (Ib), a stereoisomer, or a pharmaceutically acceptable salt thereof is provided

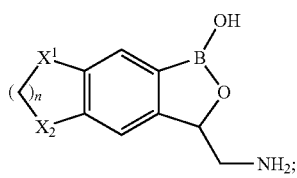

formula (Ib)

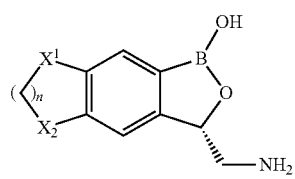

wherein $X^1$ and $X^2$, each independently represents a methylene group or oxygen atom and n represents 1 or 2.

In yet another preferred embodiment, a compound of formula (Ic), a stereoisomer, or a pharmaceutically acceptable salt thereof is provided

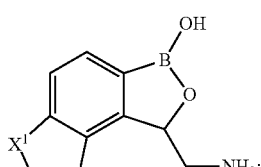

formula (Ic)

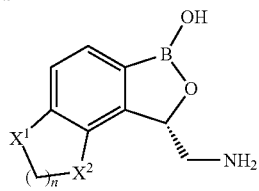

wherein $X^1$ and $X^2$, each independently represents a methylene group or oxygen atom and n represents 1 or 2.

The present invention intends to include within the scope of the first aspect, various preferred embodiments for perfecting the invention as pointed out in the background section. For example, in a preferred embodiment, one of $X^1$ and $X^2$ represents a methylene group, the other one represents oxygen atom and n is 1.

In another preferred embodiment, one of $X^1$ and $X^2$ represents a methylene group, the other one represents oxygen atom and n represents 2.

In another preferred embodiment, both $X^1$ and $X^2$ represent oxygen atom and n represents 1.

In another preferred embodiment, both $X^1$ and $X^2$ represent oxygen atom and n represents 2.

In another preferred embodiment, both $X^1$ and $X^2$ represent methylene group and n represents 1.

In yet another preferred embodiment, both $X^1$ and $X^2$ represent methylene group and n represents 2.

The present invention may involve one or more of the following embodiments associated with first aspect of the present invention. For example, in one embodiment, there is provided a compound of formula (Ia), a stereoisomer, a pharmaceutically acceptable salt thereof, wherein $X^1$ and $X^2$, each independently represents a methylene group or oxygen atom and n represents 1 or 2.

In another embodiment, there is provided a compound of formula (Ib), a stereoisomer, a pharmaceutically acceptable salt thereof, wherein $X^1$ and $X^2$, each independently represents a methylene group or oxygen atom and n represents 1 or 2.

In another embodiment, there is provided a compound of formula (Ic), a stereoisomer, a pharmaceutically acceptable salt thereof, wherein $X^1$ and $X^2$, each independently represents a methylene group or oxygen atom and n represents 1 or 2.

In a preferred embodiment, there is provided a compound of formula (Ia), a stereoisomer, a pharmaceutically acceptable salt thereof, wherein both $X^1$ and $X^2$ represent oxygen atoms and n represents 1 or 2.

In another preferred embodiment, there is provided a compound of formula (Ib), a stereoisomer, a pharmaceutically acceptable salt thereof, wherein both $X^1$ and $X^2$ represent oxygen atoms and n represents 1 or 2.

In another preferred embodiment, there is provided a compound of formula (Ic), a stereoisomer, a pharmaceutically acceptable salt thereof, wherein both $X^1$ and $X^2$ represent oxygen atoms and n represents 1 or 2.

In another preferred embodiment, there is provided a compound of formula (Ia) or (Ib) or (Ic), a stereoisomera, or pharmaceutically acceptable salt thereof, wherein one of $X^1$ and $X^2$ represents oxygen, the other represents a methylene group, and n represents 1 or 2.

In yet another preferred embodiment, there is provided a compound of formula (Ia) or (Ib) or (Ic), a stereoisomer, or a pharmaceutically acceptable salt thereof, wherein both $X^1$ and $X^2$ represent methylene group, and n represents 1 or 2.

According to a particular embodiment of the present invention, there is provided specific compound of formula (I), which is selected from:
3-(Aminomethyl)[1,3]dioxolo[4,5-f][2,1]benzoxaborol-1(3H)-ol,
3-(Aminomethyl)-6,7-dihydro[1,2]oxaborolo[3,4-g][1,4]benzodioxin-1(3H)-ol,
3-(Aminomethyl)-3,6,7,8-tetrahydro-1H-indeno[4,5-c][1,2]oxaborol-1-ol,
3-(Aminomethyl)-6,7,8,9-tetrahydronaphtho[1,2-c][1,2]oxaborol-1(3H)-ol,
8-(Aminomethyl)[1,3]dioxolo[4,5-e][2,1]benzoxaborol-6(8H)-ol,
(8S)-8-(Aminomethyl)[1,3]dioxolo[4,5-e][2,1]benzoxaborol-6(8H)-ol,
9-(Aminomethyl)-2,3-dihydro[1,2]oxaborolo[3,4-f][1,4]benzodioxin-7(9H)-ol,
3-(Aminomethyl)-7,8-dihydro[1,2]oxaborolo[3,4-f][1,4]benzodioxin-1(3H)-ol,
3-(Aminomethyl)[1,3]dioxolo[4,5-g][2,1]benzoxaborol-1(3H)-ol,
(3S)-3-(Aminomethyl)[1,3]dioxolo[4,5-g][2,1]benzoxaborol-1(3H)-ol,
3-(Aminomethyl)-5,6-dihydrofuro[3,2-f][2,1]benzoxaborol-1(3H)-ol,
3-(Aminomethyl)-6,7-dihydrofuro[2,3-f][2,1]benzoxaborol-1(3H)-ol, or a pharmaceutically acceptable salt thereof, for instance hydrochloride salt.

The compounds of the present invention described herein may be isolated in the form of a pharmaceutically acceptable salt. It should be understood that the term "pharmaceutically acceptable salt" as used herein refers to salts that are chemically and/or physically compatible with other ingredients comprising a formulation, and/or are physiologically compatible with the recipient thereof. The compounds of the present invention have a basic group such as an amino group and accordingly their salts can be prepared by reacting with inorganic or organic acid. The examples of inorganic acid salts includes, but are not limited to, hydrochloride, hydrobromide, nitrate, perchlorate, sulfate or phosphate and organic acid salts include, but not limited to, acetate, malate, lactate, fumarate, succinate, citrate, ascorbate, tartrate, oxalate, glycolate, mesylate or maleate. The term "pharmaceutically acceptable" as used herein refers to a compound of formula (I) or pharmaceutical composition thereof suitable for administration to animals, preferably humans as approved by a regulatory agency such as European Medicine Agency (EMEA), US Food and Drug Administration (FDA) or any other National Regulatory Agency.

The compound of the general formula (I) or a pharmacologically acceptable salt thereof includes stereoisomers (optical isomers, enantiomers, diastereomers). Each of these optical isomers, enantiomers, diastereomers are intended to be part of the present invention.

The carbon atom in the oxaborole ring is an asymetric carbon, stereoisomers are present based on this carbon atom as follows:

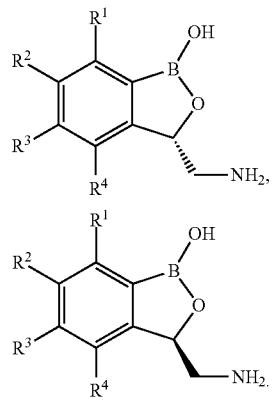

More specifically, the isomers having following structure are present for the compound of the present invention:

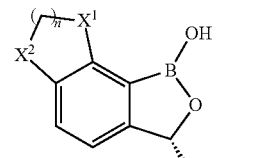

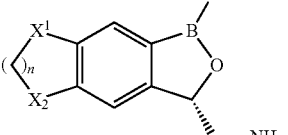

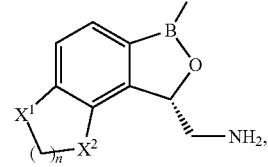

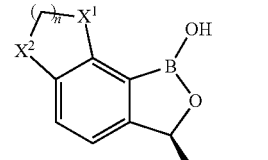

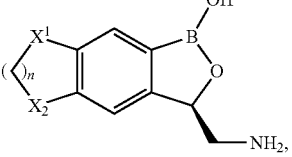

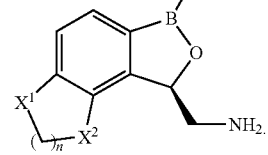

Among these, the compound of following configuration is preferable;

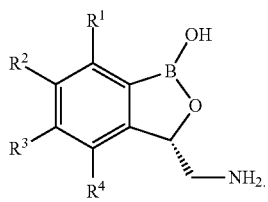

According to a particular embodiment of the present invention, there is provided specific steroisomeric compound of formula (I), which is selected from:
(8S)-8-(Aminomethyl)[1,3]dioxolo[4,5-e][2,1]benzoxaborol-6(8H)-ol hydrochloride, or
(3S)-3-(Aminomethyl)[1,3]dioxolo[4,5-g][2,1]benzoxaborol-1(3H)-ol hydrochloride,
or a pharmaceutically acceptable salt thereof, for instance hydrochloride salt.

Next, general methods of preparation of a compound of the present invention will be taken into account.

In general, compounds of the the present invention can be prepared by following general scheme and experimental procedures described hereinafter and/or by additional or alternative known processes and procedures in combination with knowledge of ordinary skill in the art. It should be understood that the methods set forth in the following general scheme are intended for illustrative purposes and are not to be construed as limiting the scope of the disclosure. In many cases, the starting materials are commercially available, however if not, they may be easily prepared by following one or more techniques known to ordinary skill in the art including, but not limited to, standard organic chemical techniques or techniques similar to the synthesis of structurally similar known compounds. The optically active form of a compound of the present invention may be obtained by any techniques know to a person of ordinary skill in the art including, for example, by resolving a racemic form of the present compound or an intermediate thereof using standard procedures, by separating a diastereoisomer or enzymatic techniques.

General Scheme

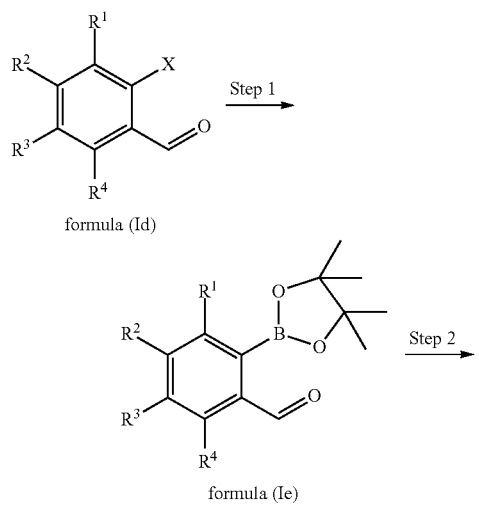

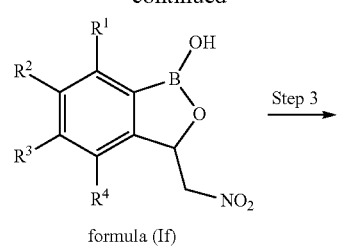

Step 1: The compound of formula (Id) can be prepared by using commercially available starting material(s) or using the procedures described hereinafter in the experimental part. The compound of formula (Ie) of the present invention can be produced by performing a borylation reaction between an aldehyde compound of formula (Id) and a borylating agent such as bis(pinacolato)diboron, bis(neopentyl glycolato)diboron or bis(catecholato)diborane in a suitable solvent such as dichloromethane, 1,4-dioxan, acetonitrile or mixture thereof in the presence of a palladium complex such as dichloro[1,1'-bis(diphenylphosphino)ferrocene]palladium(II) and a base such as potassium acetate, potassium carbonate or sodium carbonate. Such a borylation reaction can be performed in a temperature range of about 80° C. to about 110° C.

Step 2: The compound of formula (If) can be prepared by performing a reaction between an aldehyde compound formula (Ie) and aliphatic nitro compound such as nitromethane in a suitable solvent such as water, tetrahydrofuran or mixture thereof, in presence of a suitable base such as sodium bicarbonate, potassium hydroxide, sodium hydroxide or triethylamine. The compound of formula (If) can also be prepared by following scheme:

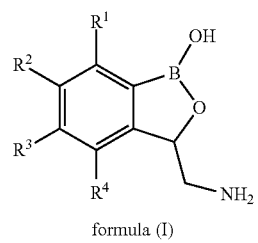

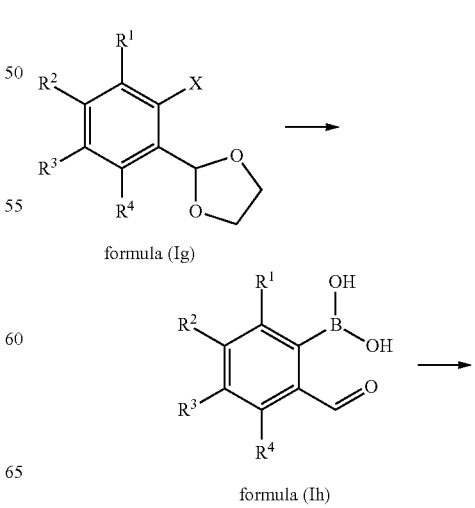

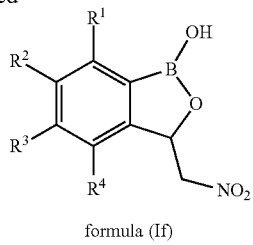

formula (If)

In the above scheme, the compound of formula (Ig) was allowed to react with boron triisopropoxide in a suitable solvent such as water, tetrahydrofuran, 1,4-dioxane or mixture thereof in the presence of an organolithium reagent such as butyllithium to give a compound formula (Ih), which upon reaction with aliphatic nitro compound such as nitromethane in a suitable solvent such as water, 1,4-dioxane, tetrahydrofuran or mixture thereof, in the presence of a suitable base such as sodium bicarbonate, potassium hydroxide or sodium hydroxide gives a compound of formula (Ih).

Step 3: The compound of formula (I) can be prepared by reducing a nitro compound of formula (If). The reduction of a nitro compound to an amine compound can be facilitated by many different reagents and reaction conditions known to a person ordinary skill in the art including, but not limited to, the reduction in hydrazine hydrate in a suitable solvent such as methanol in the presence of a catalyst such as Raney nickel.

Generally a compound of the present invention can be purified by any methods known to a person ordinary skill in the art including, for example protecting the amine part of compound of formula (I) with an amino protecting group such as tert-butyloxycarbonyl in a suitable solvent such as water, tetrahydrofuran or mixture thereof, in the presence of a base such as sodium bicarbonate, followed by reacting an amine protecting compound with an acid such as hydrochloric acid, in a suitable solvent such as dichloromethane.

In certain embodiments, it is to be understood that in place of reducing agents, solvents, amino protecting agents, organolithium reagents, and bases, optionally indicated in one or more methods described herein, other reducing agents, solvents, amino protecting agents, organolithium reagents, and bases, as described herein, can also be employed.

As a reducing agent, unless otherwise indicated, a hydrogenated complex compound, a boron-containing compound such as sodium borohydride, sodium triacetoxy borohydride or sodium cyano borohydride can be used. In addition, catalytic reduction using a metal catalyst such as palladium carbon, Raney nickel, platinum oxide or palladium black can preferably be used.

According to the present invention, the solvents, unless otherwise indicated, include polar and non-polar solvents well known in the art including polar aprotic and polar protic solvents. The examples of polar solvents include, but not limited to, methanol, ethanol, isopropyl alcohol, tert-butanol, n-butanol, acetic acid, formic acid or water, or aprotic solvent such as tetrahydrofuran, acetonitrile, dioxane, methylene chloride, dimethylsulfoxide, acetone, N,N-dimethylformamide, N,N-dimethylacetamide, ethyl acetate, 1,2-dimethoxyethane, 1,2-dichloroethane, chloroform or pyridine. Polar solvents also include a mixture of water with any of the above, or a mixture of any two or more of the above solvents. The examples of non-polar solvents include, but not limited to, toluene, benzene, chlorobenzene, xylenes and hexanes.

The term "protecting group" as used herein refers to a group used to mask or block a particular site/functional group in the preparation for a chemical transformation at a different site/functional group in a molecule. After a particular target or transformation is complete or at some specific step later in a synthetic route, the protecting group can be removed using methods well known in the art. The examples of amino protecting groups include, but not limited to, an alkoxycarbonyl group such as a tert-butoxycarbonyl group, an aralkyloxycarbonyl group such as benzyloxycarbonyl group, an acyl group such as an acetyl group, an alkyl group or aralkyl group such as a test-butyl group, a benzyl group, an ether such as a methoxymethyl group, a silyl group such as a trimethylsilyl group, an arylsulfonyl group such as p-toluenesulfonyl group or benzenesulfonyl group, and a sulfinyl group such as benzenesulfinyl group.

An organolithium reagent, unless otherwise indicated, includes, but not limited to, methyllithium, n-butyllithium, sec-butyllithium, iso-propyllithium, tert-butyllithium or phenyllithium.

According to the present invention, the palladium complex, unless otherwise indicated, includes, but not limited to, dichloro[1,1'-bis(diphenylphosphino)ferrocene]palladium (II), 1,1'-bis(diphenylphosphino)ferrocene-palladium(II)dichloride dichloromethane, dichloro{bis-2-(3,5-dimethylpyrazolyl-1-carbonyl)furan}palladium(II), dichloro{bis-2-(3,5-dimethylpyrazolyl-1-carbonyl)thiophene}palladium (11), dichloro{bis2-(3,5-di-tert-butylpyrazolyl-1-carbonyl)furan}palladium(II), dichloro{bis-2-(3,5-di-tert-butylpyrazolyl-1-carbonyl)thiophene}palladium(II), dichloro{bis-2-(3-methylpyrazolyl-1-carbonyl)-furan}palladium(II), dichloro{bis-2-(pyrazolyl-1-carbonyl)furan}palladium(II), dichloro{bis-2-(3,5-diphenylpyrazolyl-1-carbonyl)furan}palladium(II) and dichloro{bis-2-(3,5-diphenylpyrazolyl-1-carbonyl)thiophene}palladium(II).

Base, unless otherwise indicated, includes, but not limited to, potassium hydroxide, sodium hydroxide, potassium carbonate, sodium carbonate, cesium carbonate, magnesium carbonate, barium carbonate, methylamine, triethylamine, diisopropylethylamine and pyridine.

In certain embodiments, it is desirable to separate the reaction products from one another and/or from a starting material to get the desired product in a purified form. Such a separation can be performed by using techniques well known in the art. For example, multiphase extraction, crystallization from a solvent or solvent mixture, distillation, sublimation or chromatography. One skilled in the art will apply the techniques most likely to achieve the desired purification.

In certain embodiments, the present invention encompasses isotopically labeled compounds of the formula (I). All isotopes of any particular atom or element as specified are contemplated within the scope of the present invention. The examples of isotopes that can be incorporated into compounds of the present invention include, but not limited to, isotopes of hydrogen (e.g., $^2$H or $^3$H), carbon (e.g., $^{13}$C or $^{14}$C), nitrogen (e.g., $^{13}$N or $^{15}$N), oxygen (e.g., $^{15}$O, $^{17}$O or $^{18}$O), phosphorous (e.g., $^{32}$P or $^{33}$P), sulphur (e.g., $^{35}$S), halogen (e.g., $^{18}$F, $^{36}$Cl, $^{123}$I or $^{125}$I). In a preferred embodiment, the present invention provides deuterium (D or $^2$H) compounds of the formula (I). Isotopically labeled compounds of formula (I) can be prepared by following the general scheme and methods thereof using isotopically labeled reagents. Isotopically labeled compounds of the present invention may be useful in compound and/or substrate tissue distribution assays. Such applications of isotopically labeled compounds are well known to a person skilled in the art, and are therefore within the scope of the present invention.

In another embodiment, the present invention includes within its scope prodrugs of compounds of this invention. In general, such prodrugs will be functional derivatives of the compounds of this invention which are readily convertible in vivo into the required compound, and should not have safety concern due to cleaved component. Conventional procedures for the selection and preparation of a suitable prodrug derivative known in the art can be used. For example, phosphates and salt thereof, esters and salt thereof, amides and salts thereof can be used for the selection of a suitable prodrug of a compound disclosed herein.

Next, a pharmaceutical composition comprising a compound of formula (I), a stereoisomer, or pharmaceutically acceptable salt thereof will be provided.

A compound of the present invention alone or in the form of a pharmaceutical composition may be typically used to prevent or treat bacterial infections in animals including humans. Thus, for treating and preventing a suitable dosage form may be required. The suitable dosage forms will depend upon the use or route of administration. Techniques and formulations generally may be found in *The Science and Practice of Pharmacy*, 21$^{st}$ edition, Lippincott, Willams and Wilkins, Philadelphia, Pa., 2005 (incorporated herein by reference).

Thus, the present invention in its another aspect provides a pharmaceutical composition comprising a compound of formula (I), a stereoisomer or a pharmaceutically acceptable salt thereof, or a prodrug of the same, and one or more pharmaceutically acceptable excipient(s).

The compound of formula (I), a stereoisomer, or a pharmaceutically acceptable salt thereof, may be administered as pharmaceutical composition in association with one or more pharmaceutically acceptable excipient(s). The term "excipient" as used herein refers to any ingredient in the formulation other than a compound of formula (I), pharmaceutically acceptable salt or stereoisomer thereof. The examples of excipients include, but not limited to, carriers, vehicles, solvents, adjuvants, lubricants, surfactants, binders, buffers, diluents, flavouring agents, coloring agents, disintegrants, emulsifying agents, suspending agents, solubilizers, fillers or bulking agents. The choice of excipient(s) will largely depend on factors such as mode of administration, effect of an excipient on solubility, stability, and release profile, and nature of a dosage form. The compound of formula (I), pharmaceutically acceptable salt or stereoisomer thereof may be generally referred to as the active ingredient in a pharmaceutical composition.

A pharmaceutical composition suitable for the delivery of a compound of formula (I) and methods for their preparation will be readily apparent to those skilled in the art. Such compositions and methods for their preparation may be found, for example, in *Remington's Pharmaceutical Sciences*, 19$^{th}$ ed., (Mack Publishing Company, 1995).

The compounds can be administered by different routes including, for example intravenous, intraperitoneal, subcutaneous, intramuscular or oral. For intravenous administration, the compound of formula (I), stereoisomer, or a pharmaceutically acceptable salt thereof can be formulated as a sterile solution, suspension or emulsion, and for oral administration as a tablet, capsule (hard or soft filled), pill, powder, sustain or immediate release formulation, solution or suspension.

The amount of active ingredient(s) and excipient(s) to be present in a pharmaceutical composition can be determined by standard procedures taking into account various factors including, but not limited to, IC$_{50}$ or half life of the compound; age, size and weight of the patient; the disease state associated with the patient. The importance of these and other factors are well known to those of ordinary skill in the art. Generally, a dose will be upto 15000 mg/day While certain dose and administration regimens are exemplified herein, however, these do not in any way limit the dose and administration regimen that may be provided to the patient in practicing the present invention.

The compounds of the present invention have therapeutic applications and may be used to treat or prevent bacterial infections caused by Gram-negative bacteria and resistant bacteria thereof.

Thus, the present invention in its another aspect provides a method for treating or preventing bacterial infections in a patient comprising administering to the said patient a therapeutically effective amount of a compound of formula (I), a stereoisomer, or a pharmaceutically acceptable salt thereof, or a pharmaceutical composition containing the same.

Another aspect of the present invention provides the use of a compound of formula (I), a stereoisomer, or a pharmaceutically acceptable salt thereof, for the manufacture of a medicament for preventing and/or treating bacterial infections.

As used herein the term "therapeutically effective amount" refers to the amount of a compound of the present invention, when administered to a patient for treating or preventing bacterial infections, is sufficient to effect such treatment or prevention.

As used herein the term "patient" refers to a subject such as human suffering from bacterial infection as defined hereinafter and needs therapeutic intervention for the treatment and/or prevention of such bacterial infection.

As used herein the term "medicament" refers to a medicine or agent in a specified formulation, which promotes recovery from the bacterial infections as discussed herein.

As used herein the term "Gram-negative bacteria" refers, but not limited to, *Acinetobacter baumannii, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter coli, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vul-*

*nificus, Vibrio alginolyticus, Yersinia enterocolitica, Yersinia pestis, Yersinia pseudotuberculosis, Chlamydophila pneumoniae, Chlamydophila trachomatis, Ricketsia prowazekii, Coxiella bumetii, Ehrlichia chafeensis* or *Bartonella hensenae*. In a preferred embodiment of the present invention, the Gram-negative bacteria is selected from *Acinetobacter baumannii, Escherichia coli, Klebsiella pneumoniae* or *Pseudomonas aeruginosa*.

In another embodiment of the present invention, there is provided a method for treating infectious diseases especially caused by a pathogen selected from *Escherichia coli, Klebsiella pneumoniae* or *Pseudomonas aeruginosa*.

In further embodiment of the present invention, there is provided a method for treating infectious diseases caused by Gram-negative bacteria or resistant bacteria thereof.

As mentioned above, the compounds of the present invention will be useful in treating or preventing bacterial infection. Thus, in one embodiment, the bacterial infection may refer, but not limited to, complicated and uncomplicated urinary tract infection, hospital-acquired pneumonia, osteomyelitis, syphilis, intra-abdominal infections, nosocomial pneumonia, bacteremia, gynecological infection, respiratory tract infection, acute exacerbation of chronic bronchitis, cystic fibrosis, acute otitis media, acute sinusitis, catheter-related sepsis, *chlamydia*, community-acquired *pneumoniae*, endocarditis, febrile neutropenia, meningitis, gonococcal cervicitis, gonococcal urethritis, cystitis, pyelonephritis.

In another embodiment the bacterial infection may refer to intra-abdominal infections, complicated urinary tract infections, nosocomial pneumonia or bacteremia.

In a preferred embodiment of the present invention, the bacterial infection is intra-abdominal infections.

In another preferred embodiment of the present invention, the bacterial infection is complicated urinary tract infection.

In yet another preferred embodiment of the present invention, the bacterial infection is nosocomial pneumonia.

It has been found that the oxaborole compounds bind to editing site of leucyl-tRNA synthetase (LRS enzyme), and the resistance to oxaborole compounds occurs due to changes in amino acids at editing site. Such editing defective mutants cannot discriminate between leucine and leucine analogs like norvaline. The inventors of the present invention had observed that amino acids such as norvaline, isoleucine, norleucine, valine, analogs thereof, or salts thereof inhibits growth of oxaborole resistant mutants. Hence, the present invention in its another embodiment provides a combination of a compound of formula (I) with such amino acids or salts thereof for treatment of bacterial infections as described hereinbefore.

Next, experimental procedures for the preparation of a compound of formula (I) and intermediates thereof will be provided.

Experimental Procedures

It should be understood that the procedures set forth below are intended for illustrative purposes and are not to be construed as limiting the scope of the disclosure. Any modification in the procedures described herein, other synthetic procedures and modification thereon can be employed or adapted. All such modifications and alternative procedures are within the spirit and scope of the present application. In examples mentioned below, the term intermediate in some cases may refer to starting material for the synthesis of the final compound.

The examples set forth disclose yield of the final compound, which is not always necessarily the maximum value achievable, but shown only as an example. For the purpose of structural determination of final product of the present invention, the inventors relied on NMR, which refers to proton magnetic resonance spectrum and mass spectrum such as ESI method, and various other data such as IR spectrum, optical rotation, etc. Wherever possible, intermediate was also purified and structurally determined before taking to next step of the reaction. In the present application, the chemical shift in $^1$H-NMR is expressed in ppm (on δ scale) relative to tetramethylsilane as internal standard, whereas the coupling constant (J) and peak multiplicity have been referred to as singlet (s); doublet (d); doublet of doublet (dd); triplet (t); multiplet (m); broad (br) and broad singlet (bs). ACD Labs 12.0 (Version 12.5) was used for generating nomenclature of compounds and intermediates as disclosed herein.

(Example 1) Synthesis of 3-(aminomethyl)[1,3]dioxolo[4,5-f][2,1]benzoxaborol-1(3H)-ol hydrochloride (Compound 1)

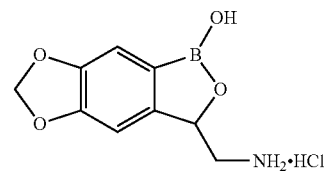

(Step 1) Synthesis of 6-(4,4,5,5-tetramethyl-1,3,2-dioxaborolan-2-yl)-1,3-benzodioxole-5-carboxaldehyde (1b)

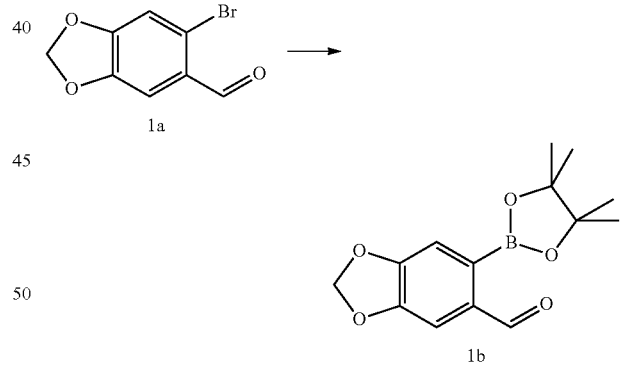

To a solution of 6-bromo-1,3-benzodioxole-5-carboxaldehyde (1a, 1.0 g, 4.86 mmoles) in 1,4-dioxane (25 mL) was added bis(pinacolato)diboron (1.66 g, 6.54 mmoles) and potassium acetate (1.28 g, 13.1 mmoles) at an ambient temperature with stirring. This mixture was degassed with argon for about 5-30 minutes and 1,1'-bis(diphenylphosphino)ferrocene]dichloropalladium(II) complex (0.284 g, 0.35 mmoles) with dichloromethane was added. The reaction mixture was heated at about 80 to 100° C. for about 4 to 6 hours. The reaction mixture was cooled to room temperature, filtered over celite pad, and washed with ethyl acetate. The organic layer was washed with water, brine, dried over anhydrous sodium sulphate and concentrated under reduced pressure. The crude product was purified by silica gel column chromatography (100-200 mesh silica gel; 20% ethyl acetate in hexane) to obtain 1.0 g (83%) of the title compound as white solid.

¹H-NMR (400 MHz, CDCl₃) δ ppm: 10.51 (s, 1H), 7.46 (s, 1H), 7.31 (s, 1H), 6.05 (s, 2H), 1.36 (s, 12H).

Mass spectrum (ESI): m/z 277.64 (M+H).

(Step 2) Synthesis of 3-(nitromethyl)[1,3]dioxolo[4,5-f][2,1]benzoxaborol-1(3H)-ol (1c)

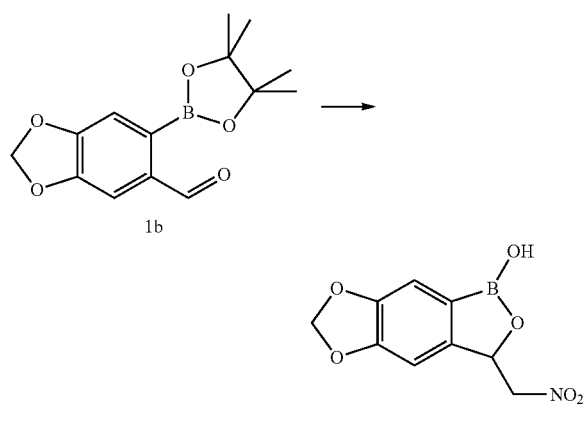

To a solution of compound 1b (2.0 g, 7.24 mmoles) in tetrahydrofuran and water (10 mL each) was added nitromethane (1.21 mL, 21.7 mmoles), cooled to 0° C., followed by addition of sodium hydroxide (0.29 g, 7.24 mmoles). The reaction mixture was stirred at room temperature for about 5-6 hours. The pH of reaction mixture was adjusted to about 3 by addition of hydrochloric acid (2N). The title compound was precipitated as a yellow solid, filtered and washed with diethyl ether and hexane to obtain 1.7 g (99%) of the title compound.

¹H-NMR (400 MHz, DMSO-d₆) δ ppm: 9.31 (s, 1H), 7.13 (s, 2H), 6.08 (s, 2H), 5.63 (dd, 1H, J=3.0 Hz, 10 Hz), 5.30 (dd, 1H, J=3 Hz, 13 Hz), 4.53-4.47 (m, 1H).

(Step 3) Synthesis of 3-(aminomethyl)[1,3]dioxolo[4,5-f][2,1]benzoxaborol-1(3H)-ol hydrochloride To a solution of compound 1c (200 mg, 0.84 mmoles) in methanol (100 mL) was added Palladium-carbon (50 mg, 10%) and shaken in an atmosphere of hydrogen in Parr shaker at about 40-50 psi at room temperature for about 7 to 8 hours. The reaction mixture was filtered through celite, concentrated under reduced pressure, followed by addition of hydrochloric acid (4M) in dioxane at room temperature and stirring for few minutes. Diethyl ether was added to precipitate the product, which was filtered, washed with diethyl ether and dried to obtain 70 mg (34%) of the title compound as a white solid.

¹H-NMR (400 MHz, DMSO-d₆) δ ppm: 9.10 (bs, 1H), 7.12 (s, 1H), 7.04 (s, 1H), 6.05 (d, 2H, J=4.0 Hz), 5.02-4.96 (m, 1H), 3.09 (dd, 1H J=4.0, 14.0 Hz), 2.68-2.62 (m, 1H).

Mass spectrum (ESI): m/z 208.49 (M+H).

(Example 2) Synthesis of 3-(aminomethyl)-6,7-dihydro[1,2]oxaborolo[3,4-g][1,4]benzodioxin-1(3H)-ol hydrochloride (Compound 2)

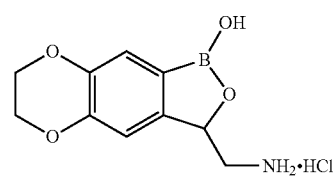

(Step 1) Synthesis of 2,3-dihydro-1,4-benzodioxine-6-carboxaldehyde (2b)

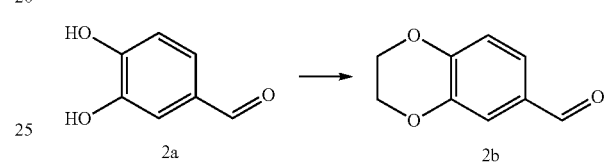

The compound 2b was synthesized following procedure disclosed in WO 2005/105753.

(Step 2) Synthesis of 7-bromo-2,3-dihydro-1,4-benzodioxine-6-carboxaldehyde (2c)

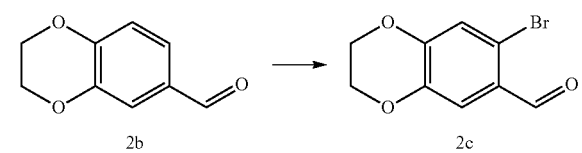 [SMILES: O=Cc1ccc2c(c1)OCCO2 ; O=Cc1cc2c(cc1Br)OCCO2]

To a solution of compound 2b (3.5 g, 21.3 mmoles) in methanol (100 mL) was added bromine (4.07 g, 25.6 mmoles) at room temperature. The reaction mixture was stirred at the same temperature for about 3 hours. The reaction mixture was concentrated and diluted with ethyl acetate and water. The ethyl acetate layer was separated, dried over anhydrous sodium sulphate and concentrated under reduced pressure. The crude product was subjected to column chromatography (100-200 mesh silica gel, 20% ethyl acetate in hexane) to obtain 3.3 g (64%) of the title compound as yellow solid.

¹H-NMR (400 MHz, CDCl₃) δ ppm: 8.41 (s, 1H), 7.45 (s, 1H), 7.14 (s, 1H), 4.34-4.25 (m, 4H).

(Step 3) Synthesis of 7-(4,4,5,5-tetramethyl-1,3,2-dioxaborolan-2-yl)-2,3-dihydro-1,4-benzodioxine-6-carboxaldehyde (2d)

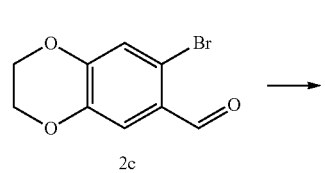

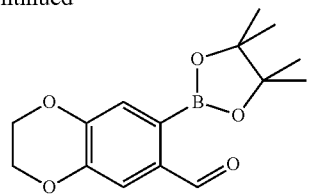

2d

To a solution of compound 2c (500 mg, 2.06 mmoles) in 1,4-dioxane (8 mL), was added bis(pinacolato)diboron (1.04 g, 4.12 mmoles) and potassium acetate (606 mg, 6.18 mmoles) at room temperature with stirring. This mixture was degassed with argon for 5-30 min and 1,1'-bis(diphenylphosphino)ferrocene]dichloropalladium(II) dichloromethane complex (134 mg, 0.165 mmoles) was added. The resulting reaction mixture was heated at about 80 to 100° C. for about 3 hours. The reaction mixture was cooled to room temperature, filtered over celite pad, and washed with ethyl acetate. The organic layer was washed with water, brine, dried over anhydrous sodium sulphate and concentrated under reduced pressure. The crude product was purified by silica gel column chromatography (100-200 mesh silica gel, 0 to 10% ethyl acetate in hexane) to obtain 200 mg (34%) of the title compound as a white solid.

$^1$H-NMR (400 MHz, CDCl$_3$) δ ppm: 10.45 (s, 1H), 7.52 (s, 1H), 7.38 (s, 1H), 4.32-4.28 (m, 4H), 1.36 (s, 12H).

Mass spectrum (ESI): m/z 291.96 (M+H).

(Step 4) Synthesis of 3-(nitromethyl)-6,7-dihydro[1,2]oxaborolo[3,4-g][1,4]benzodioxin-1(3H)-ol (2e)

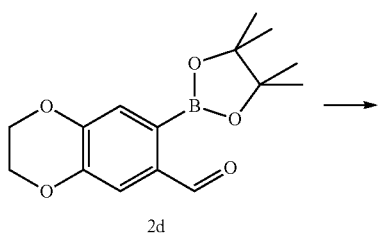

To a solution of compound 2d in dioxane and water (1.5 mL each), were added triethylamine (0.095 mL, 0.69 mmoles) and nitromethane (0.026 mL, 0.48 mmoles) and stirred at room temperature for about 1 hour. The pH of the reaction mixture was adjusted to about 3 by addition of hydrochloric acid (2N). The reaction mixture was extracted with ethyl acetate, washed with water, brine, dried over anhydrous sodium sulphate and concentrated under reduced pressure. The crude product thus formed was subjected to column chromatography (100-200 mesh silica gel, 0 to 20% ethyl acetate in hexane) to obtain 70 mg (41%) of title compound as off white solid.

$^1$H-NMR (400 MHz, DMSO-d$_6$+D$_2$O) δ ppm: 7.19 (s, 1H), 7.06 (s, 1H), 5.63-5.65 (m, 1H), 5.23 (m, 1H), 4.45-4.51 (m, 1H), 4.25-4.26 (m, 4H).

Mass spectrum (ESI): m/z 250 (M−H).

(Step 5) Synthesis of 3-(aminomethyl)-6,7-dihydro[1,2]oxaborolo[3,4-g][1,4]benzodioxin-1(3H)-ol (2f)

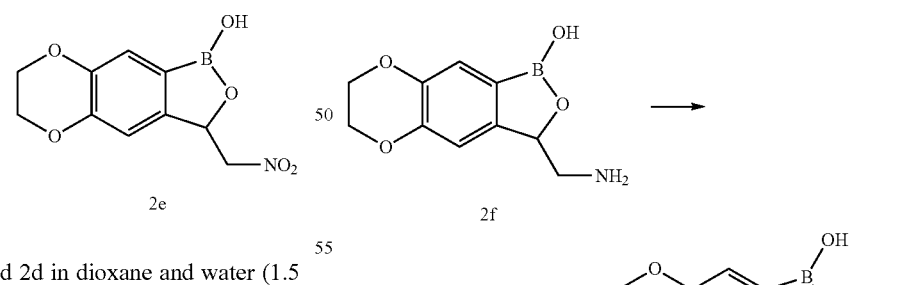

To a suspension of compound 2e (170 mg, 0.68 mmoles) in methanol (7 mL), was added Raney nickel (20 mg), cooled to 0° C., followed by dropwise addition of hydrazine hydrate (99%, 0.1 mL, 2.04 mmoles). The effervescence was observed and reaction mixture was allowed to warm to room temperature and kept at the same temperature for about 1 hour. The Raney nickel was filtered over celite, washed with methanol and combined filtrate was evaporated under reduced pressure to give crude compound, which was triturated with diethyl ether and dried to obtain 100 mg (67%) of the title compound.

This crude product was used as such for next step.

(Step 6) Synthesis of tert-butyl [(1-hydroxy-1,3,6,7-tetrahydro[1,2]oxaborolo[3,4g][1,4]benzodioxin-3-yl)methyl]carbamate (2g)

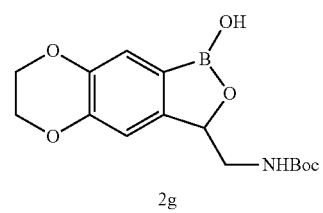

Sodium bicarbonate (263 mg, 3.16 mmoles) was added to compound 2f (140 mg, 0.63 mmoles) dissolved in tetrahydrofuran and water (1.5 mL each). Di-tert-butyl dicarbonate (275 mg, 1.26 mmole) was added and reaction mixture was stirred at room temperature for about 2 hours. The ethyl acetate and water were added to the reaction mixture. The organic layer was separated. The combined organic extracts were again washed with water and brine solution, dried over anhydrous sodium sulphate and evaporated under reduced pressure to obtain the crude compound, which was purified by preparatory thin layer chromatography (30% ethyl acetate in hexane) to obtain 59 mg (29%) of the title compound.

$^1$H-NMR (400 MHz, DMSO-$d_6$+$D_2O$) δ ppm: 7.16 (s, 1H), 6.86 (s, 1H), 5.01-4.98 (m, 1H), 4.27-4.19 (m, 4H), 3.28 (dd, 1H, J=4.7 Hz, 13.9 Hz), 3.05 (dd, 1H, J=7.0 Hz, 13.7 Hz), 1.36 (s, 9H).

Mass spectrum (ESI): m/z 322 (M+H).

(Step 7) Synthesis of 3-(aminomethyl)-6,7-dihydro [1,2]oxaborolo[3,4-g][1,4]benzodioxin-1(3H)-ol hydrochloride To a solution of compound 2 g (55 mg, 0.171 mmoles) in dichloromethane was added hydrochloric acid (4M) in dioxane (2 mL) at room temperature. The reaction mixture was stirred at the same temperature for about half an hour. The solvents were evaporated under reduced pressure, and the solid was triturated with diethyl ether and diethyl ether was decanted. The solid thus formed was dried in vacuo to obtain 18 mg (41%) of the title compound as a white solid.

$^1$H-NMR (400 MHz, DMSO-$d_6$+$D_2O$) δ ppm: 7.25 (s, 1H), 7.03 (s, 1H), 5.21 (dd, 1H, J=2.6 9.0 Hz), 4.31-4.21 (m, 4H), 3.47-3.40 (m, 1H), 2.78-2.71 (m, 1H).

Mass spectrum (ESI): m/z 222.08 (M+H).

(Example 3) Synthesis of 3-(aminomethyl)-3,6,7,8-tetrahydro-1H-indeno[4,5-c][1,2]oxaborol-1-ol hydrochloride (Compound 3)

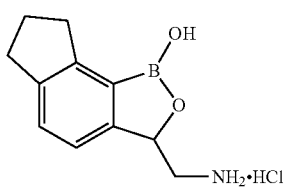

(Step 1) Synthesis of 4-hydroxy-2,3-dihydro-1H-indene-5-carboxaldehyde (3b)

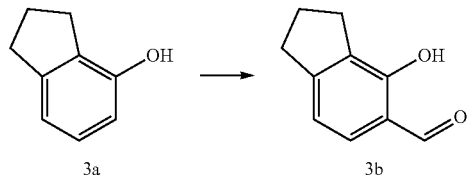 [SMILES: Oc1cccc2c1CCC2 ; O=Cc1ccc2c(c1O)CCC2]

Magnesium chloride (5.67 g, 59.6 mmoles), paraformaldehyde (2.68 g, 89.4 mmoles), triethylamine (6.02 g, 59.6 moles) were mixed in tetrahydrofuran (20 mL) and stirred at room temperature for about 15 minutes. The compound 3a (4 g, 29.8 mmoles) was added to the reaction mixture and stirred at 75° C. for about 4 hours. The reaction mixture was cooled to room temperature and hydrochloric acid (1N) was added, followed by extraction with ethyl acetate. The crude product was purified by flash chromatography (20% ethyl acetate in hexane) to obtain 2.6 g (54%) of the title compound as white solid.

$^1$H-NMR (400 MHz, CDCl$_3$) δ ppm: 11.0 (s, 1H), 9.84 (s, 1H), 7.35 (d, 1H, J=7.6 Hz), 6.90 (d, 1H, J=7.6 Hz), 2.98-2.89 (m, 4H), 2.13 (p, 2H) Mass spectrum (ESI): m/z 163.06 (M+H), 161.12 (M−H).

(Step 2) Synthesis of 5-formyl-2,3-dihydro-1H-inden-4-yl trifluoromethanesulfonate (3c)

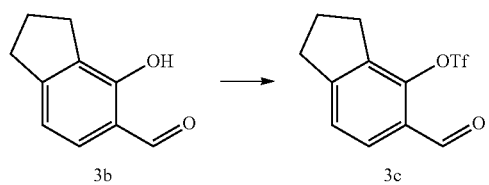 [SMILES: O=Cc1ccc2c(c1O)CCC2 ; O=Cc1ccc2c(c1OS(=O)(=O)C(F)(F)F)CCC2]

To a solution of compound 3b (2.6 g, 16 mmoles) in dichloromethane (30 mL) was added pyridine (3.17 g, 40 mmoles) at room temperature. The reaction mixture was cooled to 0° C. and triflic anhydride (6.38 g, 22.5 mmoles) was added dropwise. The reaction mixture was stirred at 0° C. for about 2 hours. Dichloromethane (100 mL) was added to the reaction mixture and washed with hydrochloric acid (1N). The organic layer was dried over anhydrous sodium sulphate, concentrated to obtain 5.6 g of the title compound as reddish oil.

This compound was used directly in next step.

(Step 3) Synthesis of 4-(4,4,5,5-tetramethyl-1,3,2-dioxaborolan-2-yl)-2,3-dihydro-1H-indene-5-carboxaldehyde (3d)

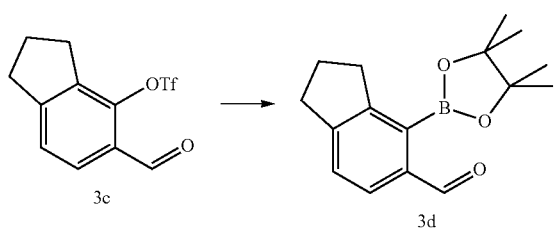 [SMILES: O=Cc1ccc2c(c1OS(=O)(=O)C(F)(F)F)CCC2 ; CC1(C)OB(c2c(C=O)ccc3c2CCC3)OC1(C)C]

The compound 3d (8 g crude yellow semisolid) was synthesized in a similar manner as described in (Example 1, Step 1) using compound 3c (5.6 g, 19 mmoles), bis(pinacolato)diboron (9.67 g, 38 mmoles), potassium acetate (5.63 g, 57 mmoles), 1,1'-bis(diphenylphosphino)ferrocene]dichloropalladium(II) complex with dichloromethane (4.67 g, 5.7 mmoles). Based on thin layer chromatography, the compound 3d was directly taken to next step.

(Step 4) Synthesis of 3-(nitromethyl)-3,6,7,8-tetra-hydro-1H-indeno[4,5-c][1,2]oxaborol-1-ol (3e)

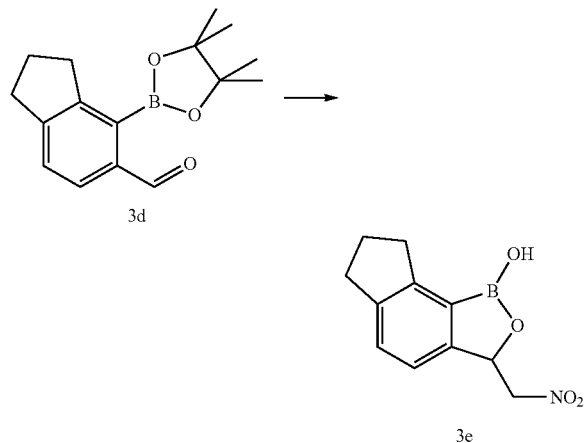

The compound 3e was prepared in the similar manner as described in (Example 1, Step 2) or (Example 2, Step 4) using compound 3d (2.0 g, 7.35 mmoles), nitromethane (1.3 g, 22.0 mmoles), sodium hydroxide (294 mg, 7.35 moles), and tetrahydrofuran (20 mL) and water (10 mL), but the compound was purified by flash chromatography (35% ethyl acetate in hexane) to obtain 250 mg, (15%) of the title compound as yellow solid.

$^1$H-NMR (400 MHz, DMSO-$d_6$) δ ppm: 9.18 (s, 1H), 7.40-7.35 (m, 1H), 7.30-7.24 (m, 1H), 5.84-5.71 (m, 1H) 5.35-5.27 (m, 1H), 4.64-4.47 (m, 1H), 2.97-2.79 (m, 4H), 2.07-1.94 (m, 2H)

Mass spectrum (ESI): m/z 232.07 (M–H).

(Step 5) Synthesis of 3-(aminomethyl)-3,6,7,8-tetra-hydro-1H-indeno[4,5-c][1,2]oxaborol-1-01 hydro-chloride

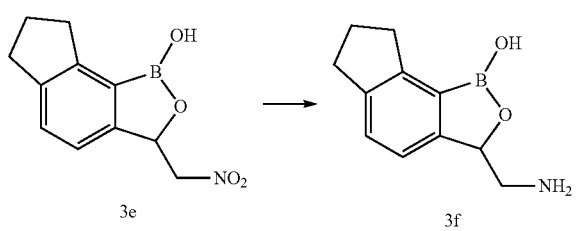 [SMILES: O=[N+]([O-])CC1OB(O)c2c1ccc1c2CCC1 ; NCC1OB(O)c2c1ccc1c2CCC1]

The hydrochloride salt of compound 3f (white solid) was prepared in the similar manner as described in (Example 1, Step 3) using a solution of compound 3f (250 mg, 1.07 mmoles) in acetic acid (5 mL) and 20% palladium hydrox-ide-carbon (125 mg, 50% moist, 2:1 w/w substrate to catalyst).

Yield: 60 mg (23%).

$^1$H-NMR (400 MHz, DMSO-$d_6$) δ ppm: 7.40 (d, 1H, J=7.6 Hz), 7.24 (d, 1H, J=7.6 Hz), 5.30 (d, 1H, J=6.9 Hz), 3.5-3.43 (m, 1H), 3.01-2.81 (m, 4H), 2.8-2.72 (m, 1H), 2.09-1.97 (m, 2H).

Mass spectrum (ESI): m/z 204.04 (M+H).

(Example 4) Synthesis of 3-(Aminomethyl)-6,7,8,9-tetrahydronaphtho[1,2-c][1,2]oxaborol-1(3H)-ol hydrochloride (Compound 4)

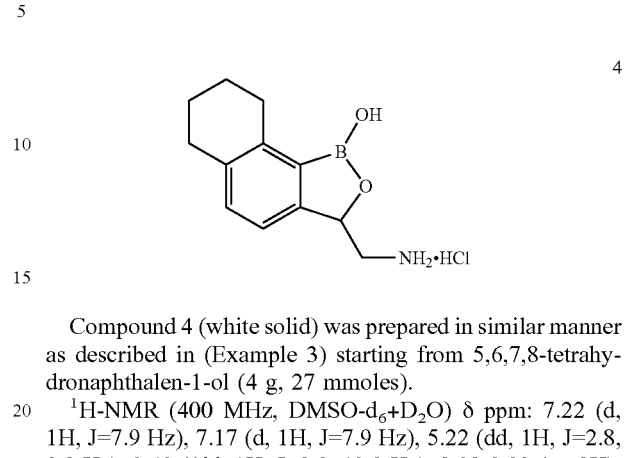

Compound 4 (white solid) was prepared in similar manner as described in (Example 3) starting from 5,6,7,8-tetrahy-dronaphthalen-1-ol (4 g, 27 mmoles).

$^1$H-NMR (400 MHz, DMSO-$d_6$+$D_2O$) δ ppm: 7.22 (d, 1H, J=7.9 Hz), 7.17 (d, 1H, J=7.9 Hz), 5.22 (dd, 1H, J=2.8, 9.2 Hz), 3.43 ((dd, 1H, J=2.9, 13.2 Hz), 2.98-2.83 (m, 2H), 2.81-2.61 (m, 3H), 1.80-1.66 (m, 4H).

Mass spectrum (ESI): m/z 217.99 (M+H).

(Example 5) Synthesis of 8-(aminomethyl)[1,3]dioxolo[4,5-e][2,1]benzoxaborol-6(8H)-ol hydro-chloride (Compound 5)

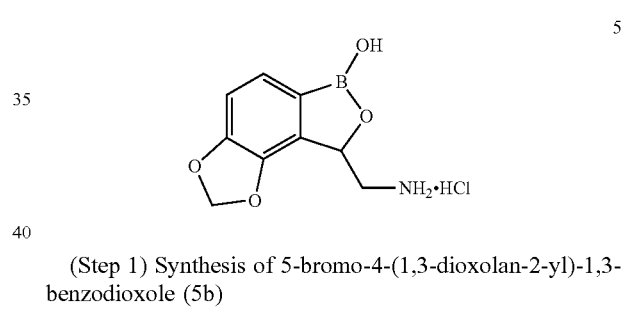

(Step 1) Synthesis of 5-bromo-4-(1,3-dioxolan-2-yl)-1,3-benzodioxole (5b)

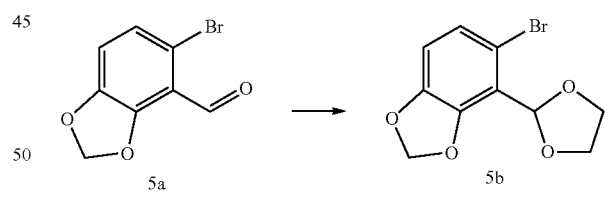

To a solution of compound 5a (500 mg, 2.18 mmoles) in toluene (15-20 mL) was added ethylene glycol (135.16 mg, 2.18 mmoles) and p-toluenesulfonic acid (83 mg, 0.44 mmoles). The resulting mixture was refluxed under Dean-Stark set up for about 12 hours. After completion of the reaction, toluene was removed and the residue was diluted with ethyl acetate. The ethyl acetate layer was neutralized with aqueous saturated sodium bicarbonate solution, sepa-rated, washed with water, dried over anhydrous sodium sulfate and concentrated under reduced pressure to obtain 355 mg (60%) of the title compound.

$^1$H-NMR (400 MHz, DMSO-$d_6$+$D_2O$) δ ppm: 7.02 (d, 1H, J=8.2 Hz), 6.68 (d, 1H, J=8.2 Hz), 6.21 (s, 1H), 6.02 (s, 2H), 4.27-4.15 (m, 2H), 4.09-3.96 (m, 2H).

(Step 2) Synthesis of (4-formyl-1,3-benzodioxol-5-yl)boronic acid (5c)

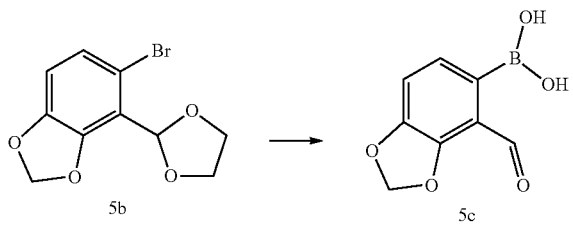 [SMILES: Brc1ccc2c(c1C1OCCO1)OCO2 ; O=Cc1c(B(O)O)ccc2c1OCO2]

To a solution of compound 5b (350 mg, 1.3 mmoles) in dry tetrahydrofuran (10 mL) at −78° C. under argon atmosphere was added n-butyllithium (94 mg, 1.47 mmoles). The resulting suspension was stirred at this temperature for about 1 hour. Boron tri-isopropoxide (722 mg, 3.84 mmoles) was then added dropwise and reaction mixture was stirred at −78° C. for about 1 hour. The solution was then allowed to warm to room temperature and was kept overnight. This reaction mixture was then cooled to 0° C. and hydrochloric acid (2N) was added. The reaction mixture was heated under reflux for about 1 hour. After cooling to room temperature, the layers were separated and the aqueous layer was extracted twice with ethyl acetate. The combined organic layer was dried over anhydrous sodium sulphate and concentrated under reduced pressure. The solid thus obtained was triturated with diethyl ether, filtered and dried to obtain 100 mg (40%) of the title compound as light brown solid.

$^1$H-NMR (400 MHz, DMSO-$d_6$) δ ppm: 10.18 (s, 1H), 7.14 (d, 1H), 7.06 (d, 1H) and 6.16 (s, 2H).

Mass spectrum (ESI): m/z 193 (M−H).

(Step 3) Synthesis of 8-(nitromethyl)[1,3]dioxolo[4,5-e][2,1]benzoxaborol-6(8H)-ol (5d)

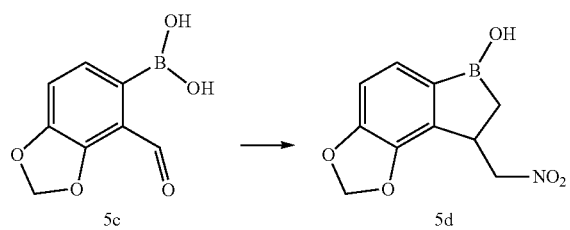 [SMILES: O=Cc1c(B(O)O)ccc2c1OCO2 ; O=[N+]([O-])CC1CB(O)c2ccc3c(c21)OCO3]

To a solution of compound 5c (100 mg, 0.5 mmoles) in tetrahydrofuran and water (1.5 mL each) were added nitromethane (31.72 mg, 0.52 mmoles), sodium bicarbonate (44 mg, 0.52 mmoles) and the reaction mixture was stirred at room temperature for about 5 hours. The pH of reaction mixture was adjusted to about 3 by addition of hydrochloric acid (2N) and extracted with ethyl acetate. The ethyl acetate layer was washed with water, brine, dried over anhydrous sodium sulphate and concentrated under reduced pressure. The crude product was purified by preparatory thin layer chromatography (30% ethyl acetate in hexane) to obtain 95 mg (78%) of the title compound as pale yellow solid.

$^1$H-NMR (400 MHz, DMSO-$d_6$) δ ppm: 9.45 (s, 1H), 7.28 (d, 1H, J=8.5 Hz), 7.03 (d, 1H, J=8.9 Hz), 6.11 (AB quartet, 2H, J=, 1 Hz, Δ=5 Hz), 5.82 (dd, 1H, J=2.8, 8.4 Hz), 5.11 (dd, 1H, J=2.8, 13.2 Hz) and 4.65-4.58 (m, 1H).

Mass spectrum (ESI): m/z 236.10 (M−H).

(Step 4) Synthesis of 8-(aminomethyl)[1,3]dioxolo[4,5-e][2,1]benzoxaborol-6(8H)-ol (5e)

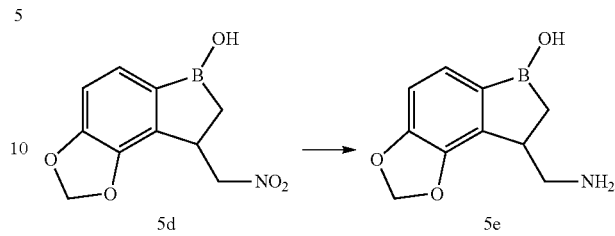

The compound 5e (Yellowish white solid) was prepared following the similar procedure as described in (Example 2, Step 5) using compound 5d (220 mg, 0.93 mmoles), Raney nickel (30 mg), hydrazine hydrate (232 mg, 4.64 mmoles). The yield of title compound was 160 mg (83%) and was taken as such for next step.

(Step 5) Synthesis of tert-butyl [(6-hydroxy-6,8-dihydro[1,3]dioxolo[4,5-e][2,1]benzoxaborol-8-yl)methyl]carbamate (5f)

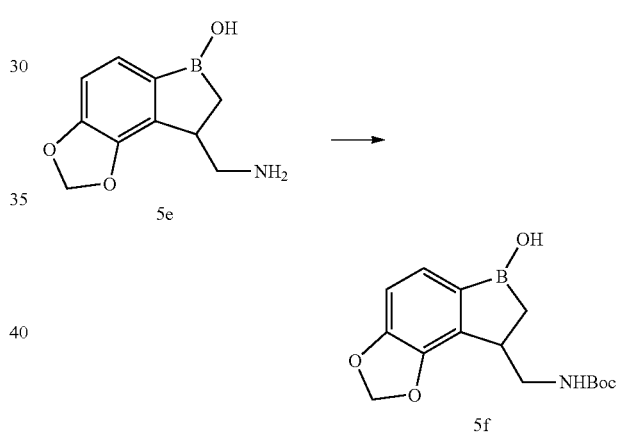

The compound 5f was synthesized following procedure described in (Example 2, Step 6) using compound 5e (160 mg, 0.77 mmoles), di-tert-butyl dicarbonate (335.72 mg, 1.54 mmoles) and sodium bicarbonate (323.4 mg, 3.85 mmoles. The crude product was purified by preparatory thin layer chromatography (25% ethyl acetate in hexane, double run) to obtain 153 mg (68%) of the title compound as off white sticky solid, which was used in next step.

(Step 6) Synthesis of 8-(aminomethyl)[1,3]dioxolo[4,5-e][2,1]benzoxaborol-6(8H)-ol hydrochloride Compound 5 (off white solid, yield: 72 mg, 61%) was synthesized following procedure described in (Example 2, Step 7) using compound 5f (150 mg, 0.49 mmoles), hydrochloric acid (4M) in dioxane (1.0 mL).

$^1$H-NMR (400 MHz, DMSO-$d_6$+$D_2O$) δ ppm: 7.35 (d, 1H, J=7.6 Hz), 7.05 (d, 1H, J=7.6 Hz), 6.11-6.09 (m, 2H,), 5.41 (dd, 1H, J=3.2, 9.2 Hz), 3.40 (dd, 1H, J=2.6, 13.2 Hz), 2.88 (dd, 1H, J=8.8, 13.2 Hz).

Mass spectrum (ESI): m/z 208.13 (M+H).

(Example 6) (8S)-8-(aminomethyl)[1,3]dioxolo[4,5-e][2,1]benzoxaborol-6(8H)-ol hydrochloride (Compound 6)

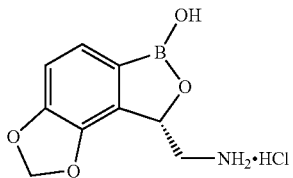

(Step 1) Synthesis of tert-butyl {[(8S)-6-hydroxy-6,8-dihydro[1,3]dioxolo[4,5-e][2,1]benzoxaborol-8-yl]methyl}carbamate Compound 5f (Example 5, Step 5) was subjected to chiral separation to obtain the chirally pure enantiomers as follows

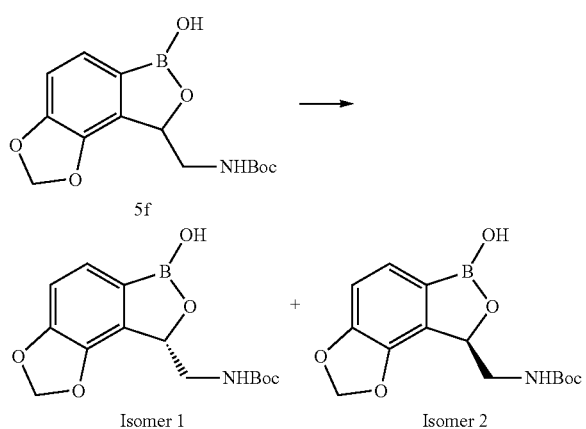

The desired isomer (isomer 1) was isolated by preparative high performance liquid chromatography using CHIRALPAK IC (4.6×250, 5μ) column; Hexane, dichloromethane, isopropanol and trifluoroacetic acid (90:05:05:0.1) as eluent with a flow rate of 1.0 mL/minute (UV: 250 nm, RT: 9.7 minutes). The configuration of active isomer was assigned based on the disclosure of WO2008/157726.

(Step 2) Synthesis of [8S)-8-(aminomethyl)[1,3]dioxolo[4,5-e][2,1]benzoxaborol-6(8H)-ol hydrochloride

[(8S)-8-(aminomethyl)[1,3]dioxolo[4,5-e][2,1]benzoxaborol-6(8H)-ol hydrochloride (off white solid) was synthesized following the procedure described in (Example 2, Step 7) using tert-butyl {[(8S)-6-hydroxy-6,8-dihydro[1,3]dioxolo[4,5-e][2,1]benzoxaborol-8-yl]methyl}carbamate (1.0 g, 3.25 mmoles), hydrochloric acid (4M) in dioxane (1.5 mL), and dichloromethane (15 mL). The reaction time was about two hours.

Yield: 790 mg.
Enantiomeric purity: 99.61%.
$^1$H-NMR (400 MHz, DMSO-$d_6$+$D_2O$) δ ppm: 7.35 (d, 1H, J=7.6 Hz), 7.05 (d, 1H, J=7.6 Hz), 6.10-6.08 (m, 2H), 5.46-5.38 (m, 1H), 3.42 (d, 1H, J=12.8 Hz), 2.94-2.84 (m, 1H)
Mass spectrum (ESI): m/z 208.22 (M+H).

(Example 7) Synthesis of 9-(aminomethyl)-2,3-dihydro[1,2]oxaborolo[4,3-f][1,4]benzodioxin-7(9H)-ol hydrochloride (Compound 7)

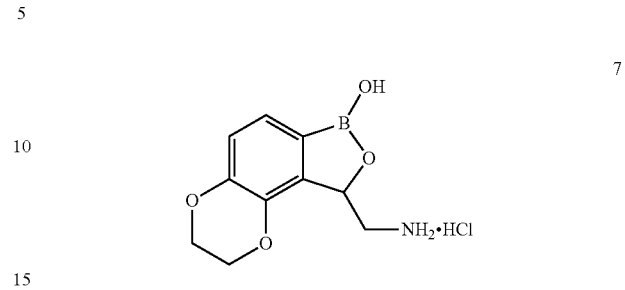

(Step 1) Synthesis of 6-bromo-2,3-dihydroxybenzaldehyde (7b)

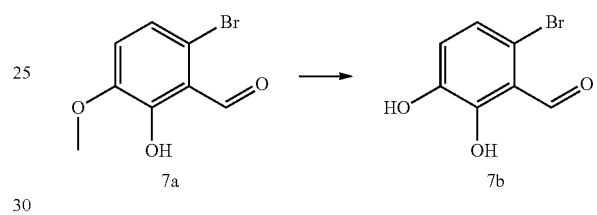

Compound 7a (5.0 g, 21.6 mmoles) was taken in dichloromethane and cooled to 0° C., followed by dropwise addition of boron tribromide (10.82 g, 43.29 mmoles). The reaction mixture was stirred at 0° C. for about 2 hours, followed by further stirring at room temperature for about 12 hours. The reaction mixture was cooled to 0° C. and neutralized with aqueous sodium bicarbonate solution, followed by dilution with dichlormethane. The organic layer was separated, dried over anhydrous sodium sulphate and concentrated under reduced pressure to obtain 4.0 g (85%) of the title compound, which was proceeded as such without any purification.

(Step 2) Synthesis of 6-bromo-2,3-dihydro-1,4-benzodioxine-5-carboxaldehyde (7c)

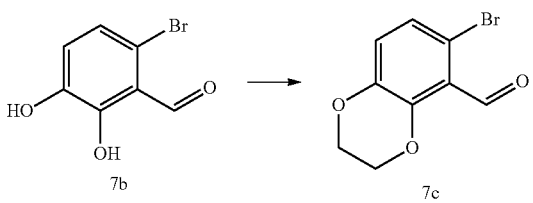 [SMILES: O=Cc1c(Br)ccc(O)c1O ; O=Cc1c(Br)ccc2c1OCCO2]

To a solution of compound 7b (2.0 g, 9.21 mmoles) in dimethylformamide (50 mL) was added cesium carbonate (8.97 g, 27.63 moles) and dibromoethane (1.89 g, 10.13 mmoles). The reaction mixture was stirred at 70° C. for about 20 hours. The reaction mixture was filtered through celite, diluted with ethyl acetate and washed with water. The organic layer was dried over anhydrous sodium sulphate and concentrated under reduced pressure. The compound thus formed was purified by column chromatography (100-200 mesh silica gel, 12% ethyl acetate in hexane) to obtain 800 mg (36%) of title compound.

$^1$H-NMR (400 MHz, DMSO-d$_6$) δ ppm: 10.22 (s, 1H), 7.18 (d, 1H, J=9.3 Hz), 7.07 (d, 1H, J=8.7 Hz), 4.38-4.34 (m, 2H), 4.33-4.29 (m, 2H).

Mass spectrum (ESI): m/z 245.09, 243.10 (bromo pattern).

(Step 3) Synthesis of 6-(4,4,5,5-tetramethyl-1,3,2-dioxaborolan-2-yl)-2,3-dihydro-1,4-benzodioxine-5-carboxaldehyde (7d)

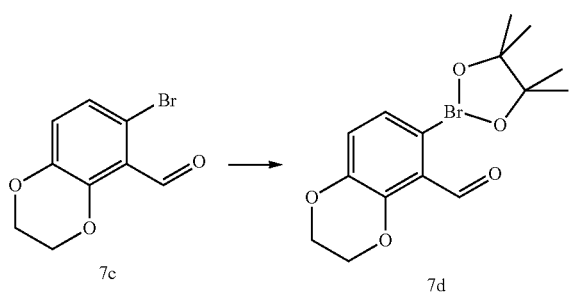

The compound 7d was prepared following procedure described in (Example 1, Step 1) using compound 7c (200 mg, 0.81 mmoles), bis(pinacolato)diboron (443 mg, 1.74 mmoles), potassium acetate (511 mg, 5.22 mmoles), 1,1-bis(diphenylphosphino)ferrocene]dichloropalladium(II) dichlormethane complex (56 mg, 0.065 mmoles). The purification was done by column chromatography (100-200 mesh silica gel, 17% ethyl acetate in hexane) to obtain 130 mg (57%) of the title compound.

$^1$H-NMR (400 MHz, CDCl$_3$) δ ppm: 10.42 (s, 1H), 7.06-7.01 (m, 2H), 4.37-4.34 (m, 2H), 4.32-4.29 (m, 2H), 1.41 (s, 12H).

Mass spectrum (ESI): m/z 291.07 (M+H).

(Step 4) Synthesis of 9-(nitromethyl)-2,3-dihydro[1,2]oxaborolo[4,3-f][1,4]benzodioxin-7(9H)-ol (7e)

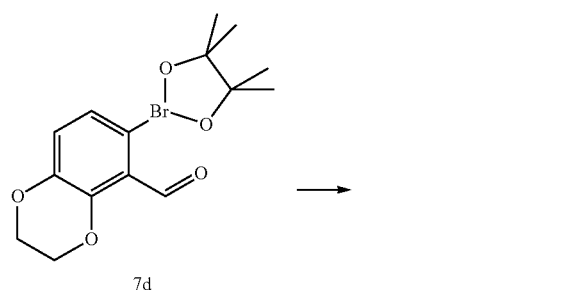

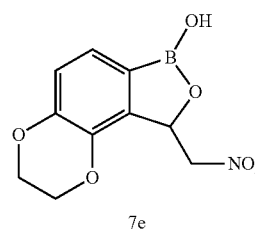

The compound 7e was prepared following procedure described in (Example 2, Step 4) using compound 7d (200 mg, 0.72 mmoles), nitromethane (43.92 mg, 0.72 mmoles) and sodium bicarbonate (60 mg, 0.72 mmoles). The reaction time was about 2.5 hours, while the purification was done by preparatory thin layer chromatography (40% ethyl acetate in hexane) to obtain 60 mg (37%) of the title compound.

$^1$H NMR (400 MHz, DMSO-d$_6$) δ ppm: 9.37 (s, 1H), 7.18 (d, 1H, J=7.6 Hz), 6.92 (d, 1H, J=7.6 Hz), 5.72 (dd, 1H, J=3.0, 9.0 Hz), 5.20 (dd, 1H, J=3.0, 13.2 Hz), 4.55-4.48 (m, 1H), 4.35-4.27 (m, 4H).

Mass spectrum (ESI): m/z 249.93 (M−H).

(Step 5) Synthesis of 9-(aminomethyl)-2,3-dihydro[1,2]oxaborolo[4,3-f][1,4]benzodioxin-7(9H)-ol (7f)

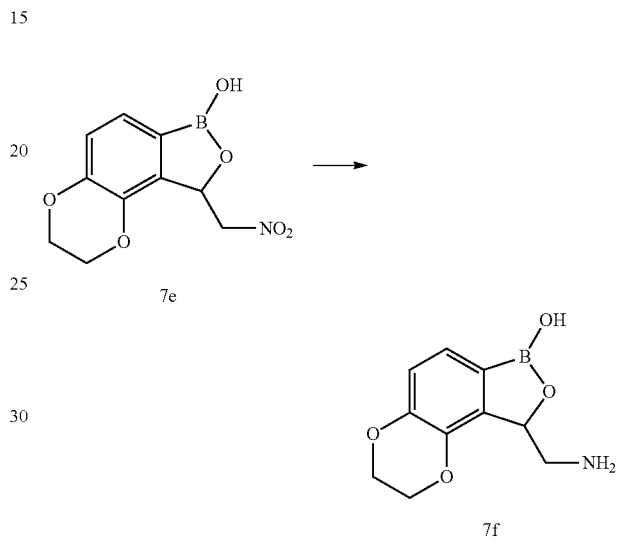

The compound 7f was prepared following procedure described in (Example 2, Step 5) using compound 7e (330 mg, 1.31 mmoles), Raney nickel (30 mg), hydrazine hydrate and methanol (10 mL). The reaction time was about 4 hours to obtain 180 mg (62%) of the title compound.

(Step 6) Synthesis of tert-butyl {[(9S)-7-hydroxy-2,3,7,9-tetrahydro[1,2]oxaborolo[4,3-f][1,4]benzodioxin-9-yl]methyl}carbamate (7g)

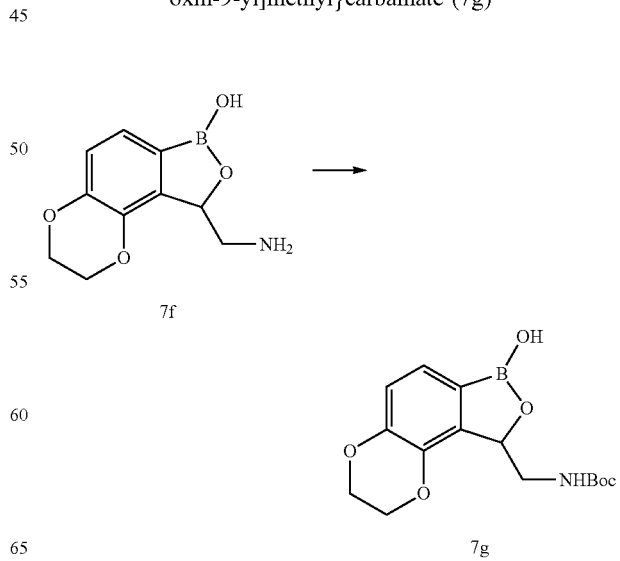

The compound 7g was prepared following procedure described in (Example 2, Step 6) using compound 7f (180 mg, 0.81 mmoles), di-tert-butyl dicarbonate (355 mg, 1.63 mmoles), sodium bicarbonate (341 mg, 4.07 mmoles), tetrahydrofuran and water (3 mL each). The reaction time was overnight while the crude product was purified by preparatory thin layer chloromatography (40% ethyl acetate in hexane) to obtain 180 mg (69%) of the title compound.

¹H-NMR (400 MHz, DMSO-d₆) δ ppm: 9.0 (s, 1H), 7.13 (d, 1H, J=8.0 Hz), 6.84 (d, 1H, J=8.0 Hz), 6.74-6.67 (m, 1H), 5.15-5.05 (m, 1H), 4.35-4.27 (m, 4H), 3.74-3.65 (m, 1H), 2.97-2.87 (m, 1H), 1.35 (s, 9H).

Mass spectrum (ESI): m/z 322.21 (M+H).

(Step 7) Synthesis of 9-(aminomethyl)-2,3-dihydro[1,2]oxaborolo[4,3-f][1,4]benzodioxin-7(9H)-ol hydrochloride Compound 7 was prepared following procedure described in (Example 2, Step 7) using compound 7g (180 mg, 0.56 mmoles), hydrochloric acid (4M) in dioxane (3 mL) and dichloromethane (4 mL). The reaction time was about 3 hours to obtain 130 mg (88%) of the title compound as off white solid.

¹H-NMR (400 MHz, DMSO-d₆+D₂O) δ ppm: 7.25 (d, 1H, J=7.8 Hz), 6.96 (d, 1H, J=7.9 Hz), 5.33 (dd, 1H, J=2.5, 8.7 Hz), 4.3 (bs, 4H), 3.52 (dd, 1H, J=2.8, 13.3 Hz), 2.87-2.77 (m, 1H).

Mass spectrum (ESI): m/z 222.15 (M+H), 219.73 (M−H).

(Example 8) Synthesis of 3-(aminomethyl)-7,8-dihydro[1,2]oxaborolo[3,4-f][1,4]benzodioxin-1(3H)-ol hydrochloride (Compound 8)

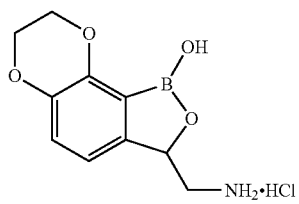

8

(Step 1) Synthesis of 2-bromo-3,4-dihydroxybenzaldehyde (8b)

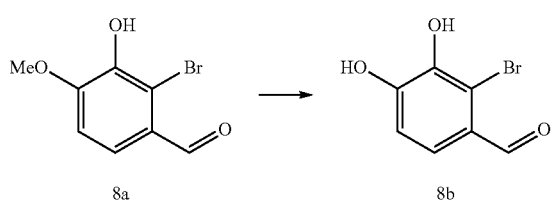 [SMILES: COc1ccc(C=O)c(Br)c1O ; O=Cc1ccc(O)c(O)c1Br]

Compound 8b was synthesized following the method described in the literature *J. Org. Chem.* 1983, 48, 2356-2360.

(Step 2) Synthesis of 5-bromo-2,3-dihydro-1,4-benzodioxine-6-carboxaldehyde (8c)

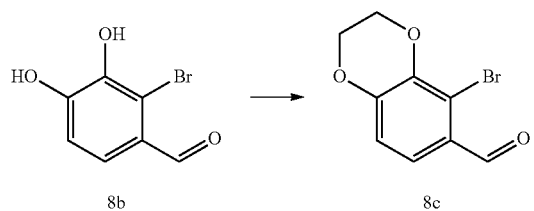 [SMILES: O=Cc1ccc(O)c(O)c1Br ; O=Cc1ccc2c(c1Br)OCCO2]

The compound 8c was prepared in a similar manner as in (Example 7, Step 1) using compound 8b (1.0 g, 4.60 mmoles), dimethylformamide (10 mL), cesium carbonate (3.0 g, 9.20 mmoles), dibromoethane (1.73 g, 9.20 mmoles). Yield: 570 mg (51%)

¹H-NMR (400 MHz, CDCl₃) δ ppm: 10.27 (5, 1H), 7.52 (d, 1H, J=8.0 Hz), 6.92 (d, 1H, J=8.5 Hz), 4.44-4.30 (m, 4H).

(Step 3) Synthesis of 5-(4,4,5,5-tetramethyl-1,3,2-dioxaborolan-2-yl)-2,3-dihydro-1,4-benzodioxine-6-carboxaldehyde (8d)

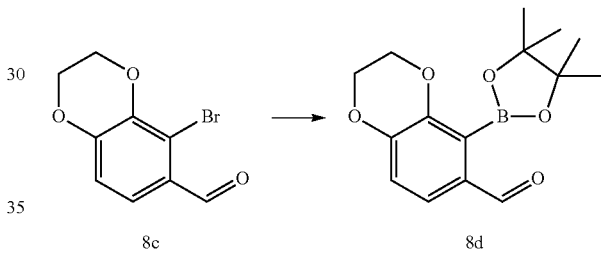

The compound 8d was synthesized in a similar manner as in (Example 1, Step 1) using compound 8c (560 mg, 2.3 mmoles), bis(pinacolato)diboron (1.14 g, 4.6 mmoles), potassium acetate (676 mg, 6.9 mmoles), 1,1'-bis(diphenylphosphino)ferrocene]dichloropalladium(II) complex dichloromethane complex (149 mg, 0.184 mmoles). The reaction time was about 9 hours, while the purification was done by flash chromatography (20% ethyl acetate in hexane) to obtain 620 mg (93%) of the title compound.

¹H-NMR (400 MHz, CDCl₃) δ ppm: 9.77 (s, 1H), 7.32 (d, 1H, J=8.0 Hz), 6.95 (d, 1H, J=8.3 Hz), 4.32-4.28 (m, 4H), 1.27 (s, 12H)

Mass spectrum (ESI): m/z 206.92 {(M-82)-1, deborylated}.

(Step 4) Synthesis of 3-(nitromethyl)-7,8-dihydro[1,2]oxaborolo[3,4-f][1,4]benzodioxin-1(3H)-ol (8e)

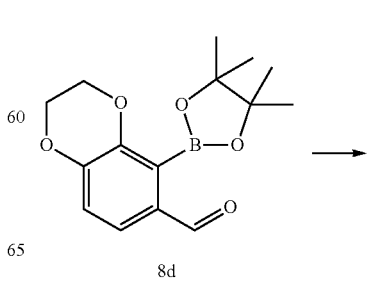

8d

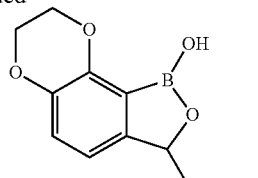

8e

The compound 8e was synthesized in similar manner as in (Example 2, Step 4) using compound 8d (620 mg, 2.13 mmoles), nitromethane (104.31 mg, 1.71 mmoles), sodium bicarbonate (142.8 mg, 1.71 mmoles), tetrahydrofuran and water (3.5 mL each). The reaction time was overnight, while the purification was done by preparatory thin layer chromatography (20% ethyl acetate in hexane) to obtain 190 mg (35%) of the title compound.

$^1$H-NMR (400 MHz, DMSO-d$_6$) δ ppm: 9.16 (S, 1H), 7.00 (d, 1H, J=7.8 Hz), 6.95 (d, 1H, J=8.0 Hz), 5.63 (dd, 1H, J=3.0, 10.0 Hz), 5.26 (dd, 1H, J=2.8, 13.2 Hz), 4.54-4.46 (m, 1H), 4.30-4.20 (m, 4H)

Mass spectrum (ESI): m/z 249.94 (M−H).

(Step 5) Synthesis of 3-(aminomethyl)-7,8-dihydro [1,2]oxaborolo[3,4-f][1,4]benzodioxin-1(3H)-ol (8f)

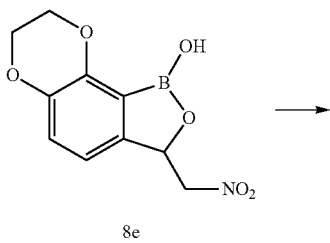

8e

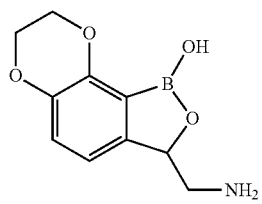

8f

The compound 8f was synthesized in a similar manner as in (Example 2, Step 5) using compound 8e (190 mg, 0.76 mmoles), Raney nickel (35 mg), hydrazine hydrate and methanol (7 mL). The reaction time was about 1 hour to obtain 130 mg (78%) of the title compound.

Mass spectrum (ESI): m/z 222.09 (M+H)

(Step 6) Synthesis of tert-butyl [(1-hydroxy-1,3,7,8-tetrahydro[1,2]oxaborolo[3,4-f][1,4]benzodioxin-3-yl)methyl]carbamate (8g)

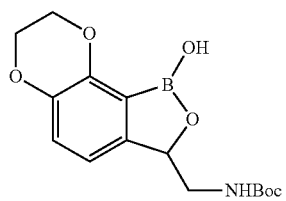

8g

The compound 8g was synthesized in a similar manner as in (Example 2, Step 6) using compound 8f (130 mg, 0.59 mmoles), di-tert-butyl dicarbonate (255.1 mg, 1.17 mmoles), sodium bicarbonate (246 mg, 2.94 mmoles), tetrahydrofuran and water (2.5 mL each). The reaction time was about 3 hours, while the purification was done by preparatory thin layer chromatography (40% ethyl acetate in hexane) to obtain 90 mg (48%) of the title compound.

$^1$H-NMR (400 MHz, DMSO-d$_6$) δ ppm: 8.86 (s, 1H), 6.94 (d, 1H, J=8.8 Hz), 6.79 (d, 1H, J=7.0 Hz), 5.03-4.95 (m, 1H), 4.29-4.17 (m, 4H), 3.34-3.29 (m, 1H), 3.04-2.93 (m, 1H), 1.37 (s, 9H).

Mass spectrum (ESI): m/z 322.09 (M+H), 320.05 (M−H).

(Step 7) Synthesis of 3-(aminomethyl)-7,8-dihydro [1,2]oxaborolo[3,4-f][1,4]benzodioxin-1(3H)-ol hydrochloride The compound 8 was synthesized in a similar manner as in (Example 2, Step 7) using compound 8g (90 mg, 0.28 mmoles), hydrochloric acid (4M) in dioxane and dichloromethane (2 mL each). The reaction time was about 1 hour to obtain 50 mg (69%) of the title compound as off white solid.

$^1$H-NMR (400 MHz, DMSO-d$_{6+}$D$_2$O) δ ppm: 7.05 (d, 1H, J=8.0 Hz), 6.93 (d, 1H, J=8.0 Hz), 5.33 (brd 1H, J=8.8 Hz), 4.34-4.18 (m, 4H), 3.47-3.36 (m, 1H), 2.84-2.69 (m, 1H).

Mass spectrum (ESI): m/z 222.15 (M+H), 220.03 (M−H).

(Example 9) Synthesis of 3-(aminomethyl)[1,3]dioxolo[4,5-g][2,1]benzoxaborol-1(3H)-ol; hydrochloride (Compound 9)

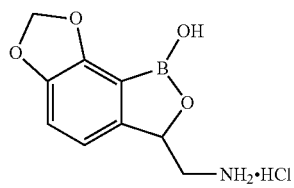

9

(Step 1) Synthesis of
4-bromo-1,3-benzodioxole-5-carboxaldehyde (9a)

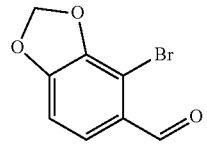

9a

The compound 9a was synthesized following the procedure described in literature in *J. Org. Chem.* 1983, 48, 2356-2360.

(Step 2) Synthesis of 4-(4,4,5,5-tetramethyl-1,3,2-dioxaborolan-2-yl)-1,3-benzodioxole-5-carboxaldehyde (9b)

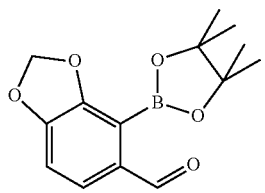

9b

The compound 9b was synthesized following the procedure described in (Example 1, Step 1) using compound 9a (1.2 g, 5.24 mmoles), bis(pinacolato)diboron (2.66 g, 10.48 mmoles), potassium acetate (1.54 g, 15.72 mmoles), 1,1'-bis(diphenylphosphino)ferrocene]dichloropalladium(II) dichloromethane complex (341 mg, 0.419 mmoles). The purification was done by flash chromatography (15% ethyl acetate in hexane) to obtain 740 mg (51%) of the title compound.

$^1$H-NMR (400 MHz, CDCl$_3$) δ ppm: 9.86 (s, 1H), 7.39 (d, 1H, J=7.9 Hz), 6.89 (d, 1H, J=7.9 Hz), 6.07 (s, 2H), 1.44 (s, 12H).

Mass spectrum (ESI): m/z 277.18 (M+H)

(Step 3) Synthesis of 3-(nitromethyl)[1,3]dioxolo[4,5-g][2,1]benzoxaborol-1(3H)-ol (9c)

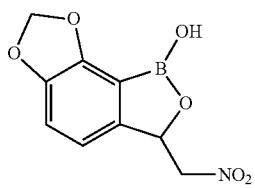

9c

The compound 9c was synthesized in a similar manner as in (Example 1, Step 2) using compound 9b (600 mg, 2.17 mmoles), nitromethane (132.37 mg, 2.17 mmoles), sodium bicarbonate (182 mg, 2.17 mmoles), tetrahydrofuran and water (7 mL each).

Yield: 200 mg (39%).

Mass spectrum (ESI): m/z 235.93 (M−H)

(Step 4) Synthesis of 3-(aminomethyl)[1,3]dioxolo[4,5-g][2,1]benzoxaborol-1(3H)-ol (9d)

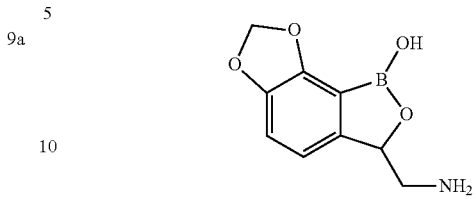

9d

The compound 9d was synthesized in a similar manner as described in (Example 2, Step 5) using compound 9c (200 mg, 0.84 mmoles), Raney nickel (about 20 mg), hydrazine hydrate and methanol (10 mL).

Yield: 120 mg (69%).

Mass spectrum (ESI): m/z 208.03 (M+H), 205.97 (M−H).

(Step 5) Synthesis of tert-butyl[(1-hydroxy-1,3-dihydro[1,3]dioxolo[4,5-g][2,1]benzoxaborol-3-yl)methyl]carbamate (9e)

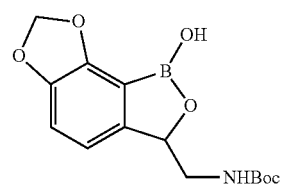

9e

The compound 9e was synthesized in a similar manner as described in (Example 2, Step 6) using compound 9d (120 mg, 0.58 mmoles), di-tert-butyl dicarbonate (251 mg, 1.15 mmoles), sodium bicarbonate (222 mg, 2.64 mmoles), tetrahydrofuran and water (4 mL each).

Yield: 40 mg (23%).

$^1$H-NMR (400 MHz, DMSO-d$_6$) δ ppm: 9.15 (s, 1H), 6.03 (s, 2H), 5.09-4.98 (m, 1H), 2.91-3.02 (m, 1H), 1.36 (s, 9H).

Mass spectrum (ESI): m/z 308.05 (M+H) 305.96 (M−H).

(Step 6) Synthesis of 3-(aminomethyl)[1,3]dioxolo[4,5-g][2,1]benzoxaborol-1(3H)-ol hydrochloride The compound 9 was synthesized in a similar manner as described in (Example 2, Step 7) using compound 9e (40 mg, 0.13 mmoles), hydrochloric acid (4M) in dioxane and dichloromethane (2 mL each).

Yield: 10 mg (32%).

$^1$H-NMR (400 MHz, DMSO-d$_6$+D$_2$O) δ ppm: 7.08 (bs, 1H), 6.96 (bs, 1H), 6.05 (bs, 2H), 5.36-5.19 (m, 1H), 3.46-3.36 (m, 1H), 2.87-2.75 (m, 1H).

$^1$H-NMR (400 MHz, DMSO-d$_6$) δ ppm: 9.43 (s, 1H), 8.05 (s, 3H), 7.08 (d, 1H, J=8.0 Hz), 6.96 (d, 1H, J=8.0 Hz), 6.07 (dd, 2H, J=1.0 Hz), 5.28 (dd, 1H, J=2.8, 8.0 Hz), 3.46-3.30 (m, 1H), 2.92-2.75 (m, 1H).

Mass spectrum (ESI): m/z 208.04 (M+H), 205.72 (M−H).

(Example 10) Synthesis of (3S)-3-(aminomethyl)[1,3]dioxolo[4,5-g][2,1]benzoxaborol-1(3H)-ol hydrochloride (Compound 10)

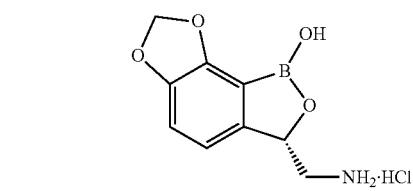

(Step 1) The compound 9c was subjected to chiral separation to obtain the chirally pure enantiomers as follows—

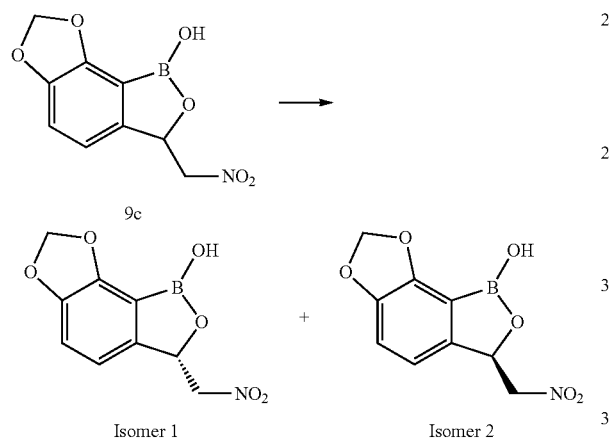

The desired isomer (isomer 1) was isolated by preparative high-performance liquid chromatography using CHIRAL-PAK AD-H, (250×50 mm 5μ) column; Methanol and trifluoroacetic acid (100:0.1) as eluent with a flow rate of 82.0 mL/minute (UV: 305 nm, RT: 5.1 minutes). The configuration of active isomer was assigned based on the disclosure of WO2008/157726.

Enantiomeric purity of active isomer 1: 99.9%
$^1$H-NMR (400 MHz, DMSO-$d_6$) δ ppm: 9.46 (s, 1H), 7.09-7.07 (d, 1H, J=7.9 Hz), 7.00-6.97 (dd, 1H, J=0.92, 7.9 Hz), 6.07-6.06 (dd, 2H, J=0.92, 3.3 Hz), 5.73-5.70 (m, 1H), 5.30-5.26 (dd, 1H, J=2.8, 13.5 Hz) 4.59-4.54 (m, 1H).
Mass spectrum (ESI): m/z 235.94 (M−H).

(Step 2) Synthesis of (3S)-3-(aminomethyl)[1,3]dioxolo[4,5-g]-[2,1]benzoxaborol-1(3H)-ol (10a)

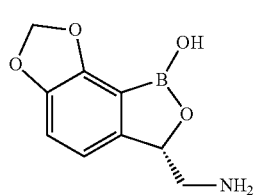

The compound 10a was synthesized in similar manner as described in (Example 2, Step 5) using corresponding nitro compound (1.0 g, 4.22 mmoles), Raney nickel (100 mg), hydrazine hydrate (3-4 mL) and methanol (40 mL). Yield: 850 mg (97%).

(Step 3) Synthesis of tert-butyl [(3S)-(1-hydroxy-1,3-dihydro[1,3]dioxolo[4,5-g][2,1]benzoxaborol-3-yl)methyl]carbamate (10b)

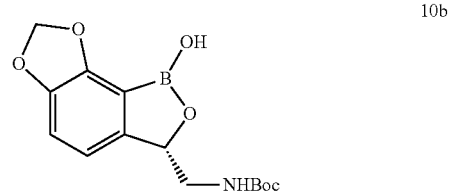 [SMILES: CC(C)(C)OC(=O)NC[C@H]1OB(O)c2c1ccc1c2OCO1]

The compound 10b was synthesized in similar manner as described in (Example 2, Step 6) using compound 10a (850 mg, 4.11 mmoles), di-tert-butyl dicarbonate (1.79 g, 8.22 mmoles), sodium bicarbonate (1.73 g, 20.55 mmoles), tetrahydrofuran and water (10 mL each). The crude product was purified by flash chromatography (55% of ethyl acetate in hexane) to obtain 750 mg (60%) of the title compound.
$^1$H-NMR (400 MHz, DMSO-$d_6$+$D_2O$) δ ppm: 7.02 (d, 1H, J=7.2 Hz), 6.84 (d, 1H, J=7.2 Hz), 6.02 (m, 2H,), 5.11-5.04 (m, 1H), 3.41-3.28 (m, 1H), 3.10-2.96 (m, 1H), 1.36 (s, 9H).
Mass spectrum (ESI): m/z 308.04 (M+H), 305.98 (M−H).

(Step 4) Synthesis of (3S)-3-(aminomethyl)[1,3]dioxolo[4,5-g][2,1]benzoxaborol-1(3H)-ol hydrochloride The compound 10 (off white solid) was synthesized in similar manner as described in (Example 2, Step 7) using compound 10b (4.0 g, 13.02 mmoles), hydrochloric acid (4M) in dioxane (25 mL) and dichloromethane (25 mL).
Yield: 2.58 g (81%).
$^1$H-NMR (400 MHz, DMSO-$d_6$+$D_2O$) δ ppm: 7.09 (d, 1H, J=8.0 Hz), 6.96 (d, 1H, J=8.0 Hz), 6.07 (bs, 2H), 5.29 (d, 1H, J=8.6 Hz), 3.42 (d, 1H, J=11.8 Hz), 2.87-2.77 (m, 1H).
Mass spectrum (ESI): m/z 208.04 (M+H), 205.83 (M−H).

(Example 11) Synthesis of 3-(aminomethyl)-5,6-dihydrofuro[3,2-f][2,1]benzoxaborol-1(3H)-ol hydrochloride (Compound 11)

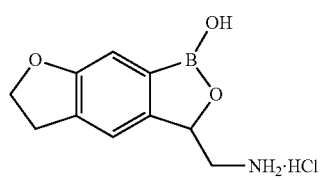

(Step 1) Synthesis of 6-hydroxy-2,3-dihydro-1-benzofuran-5-carboxaldehyde (11b)

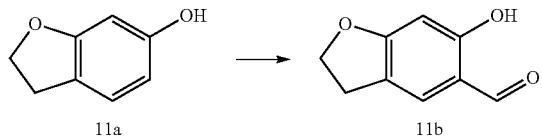 [SMILES: Oc1ccc2c(c1)OCC2 ; O=Cc1cc2c(cc1O)OCC2]

To a solution of compound 11a (commercially available, 4.5 g, 33.10 mmoles) in acetonitrile (100 mL) at room temperature were added magnesium chloride (5.67 g, 59.56 mmoles), paraformaldehyde (8.14 g, 271.43 mmoles) and N,N-diisopropylethylamine (19.21 g, 148.95 mmoles). The reaction mixture was stirred at 80° C. for about 5 to 6 hours. The reaction mixture was cooled to room temperature, diluted with ethyl acetate and washed with 5% aqueous hydrochloric acid. The organic layer was washed with water, brine, dried over anhydrous sodium sulphate and concentrated under reduced pressure. The crude product was subjected to purification by column chromatography (100-200 mesh silica gel, 0-15% ethyl acetate in hexane) to obtain 4.0 g (74%) of the title compound as yellow solid.

$^1$H-NMR (400 MHz, CDCl$_3$) δ ppm: 11.71 (5, 1H), 9.64 (s, 1H), 7.28 (t, 1H, J=1.3 Hz), 6.36 (s, 1H), 4.68 (t, 2H, J=8.6 Hz), 3.2-3.14 (m, 2H) Mass spectrum (ESI): m/z 162.98 (M−H).

(Step 2) Synthesis of 5-formyl-2,3-dihydro-1-benzofuran-6-yl trifluoromethanesulfonate (11c)

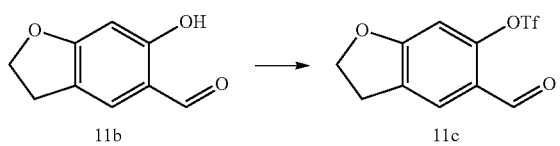 [SMILES: O=Cc1cc2c(cc1O)OCC2 ; O=Cc1cc2c(cc1OS(=O)(=O)C(F)(F)F)OCC2]

The compound 11c was prepared in similar manner as described in (Example 3, Step 2) using compound 11 b (4 g, 24.39 mmoles), triethylamine (4.93 g, 48.78 mmoles), 4-dimethylaminopyridine (40 mg), 1,1,1-trifluoro-N-phenyl-N-[(trifluoromethyl)sulfonyl]methane sulfonamide (10.44 g, 29.26 mmoles) and dichloromethane (20 mL). The reaction time was about 1 hour, while the purification was done by column chromatography (100-200 mesh silica gel, 20% ethyl acetate in hexane) to obtain 9.4 g of the title compound with 1,1,1-trifluoro-N-phenyl-N-[(trifluoromethyl)sulfonyl]methanesulfonamide impurity.

$^1$H-NMR (400 MHz, DMSO-d$_6$+D$_2$O) δ ppm: 10.10 (s, 1H), 7.82 (s, 1H), 6.76 (s, 1H), 4.78 (t, 2H, J=8.9 Hz), 3.32-3.24 (m, 2H).

Mass spectrum (ESI): m/z 296.89 (M+H).

(Step 3) Synthesis of 6-(4,4,5,5-tetramethyl-1,3,2-dioxaborolan-2-yl)-2,3-dihydro-1-benzofuran-5-carboxaldehyde (11d)

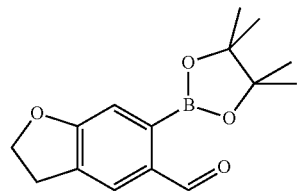

The compound 11d was synthesized in similar manner as described in (Example 1, Step 1) using compound 11c (6 g, 20.27 mmoles), bis(pinacolato)diboron (10.3 g, 40.54 mmoles), potassium acetate (5.96 g, 60.81 mmoles), 1,1'-bis(diphenylphosphino)ferrocene]dichloropalladium(II) dichloromethane complex (1.32 g, 1.62 mmoles) and dioxane (75 mL). The reaction time was about 2 hours, and the purification was done by column chromatography (100-200 mesh silica gel, 20% ethyl acetate in hexane) to obtain 5.56 g (90%) of the title compound with pinacol impurity.

$^1$H-NMR (400 MHz, DMSO-d$_6$-D$_2$O) δ ppm: 10.37 (5, 1H), 7.85 (s, 1H), 7.19 (s, 1H), 4.65 (t, 2H, J=9.2 Hz), 3.25 (t, 2H, J=8.8 Hz), 1.34 (s, 12H).

Mass spectrum (ESI): m/z 272 (M−2).

(Step 4) Synthesis of 3-(nitromethyl)-5,6-dihydrofuro[2-f][2,1]benzoxaborol-1(3H)-ol (11e)

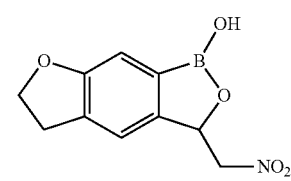

The compound 11e was synthesized in a similar manner as described in (Example 2, Step 4) using compound 11d (5 g, 18.24 mmoles), nitromethane (1.11 g, 18.24 mmoles), sodium hydroxide (729.6 mg, 18.24 mmoles), tetrahydrofuran and water (25 mL each). The reaction time was about 5 to 6 hours, and the purification was done by column chromatography (100-200 mesh silica gel, 40% ethyl acetate in hexane) to obtain 2.38 g, (56%) of the title compound with some pinacol impurity.

$^1$H-NMR (400 MHz, DMSO-d$_6$+D$_2$O) δ ppm: 7.38 (s, 1H), 7.03 (s, 1H), 5.76-5.60 (m, 1H) 5.29-5.14 (m, 1H), 4.61-4.43 (m, 3H), 3.21 (t, 2H, J=8.7 Hz).

Mass spectrum (ESI): m/z 234 (M−H).

(Step 5) Synthesis of 3-(aminomethyl)-5,6-dihydro-furo[3,2-f][2,1]benzoxaborol-1(3H)-ol (11f)

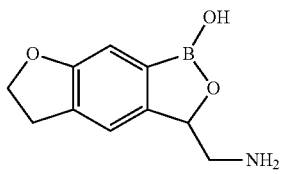

11f

The compound 11f was synthesized in similar manner as described in (Example 2, Step 5) using compound 11e (2.38 g, 10.13 mmoles), Raney nickel (230 mg), hydrazine hydrate and methanol (15 mL). The yield of the title compound was 920 mg (46%).

Mass spectrum (ESI): m/z 205.89 (M+H).

(Step 6) Synthesis of 3-(aminomethyl)-5,6-dihydro-furo[3,2-f][2,1]benzoxaborol-1(3H)-ol hydrochloride To a solution of compound 11f (20 mg) in dichloromethane (2 mL) was added hydrochloric acid (4M, 2 drops) in dioxane. The reaction mixture was stirred at room temperature for about 3 hours. The solvent was evaporated, solid so obtained was washed with diethyl ether and hexane to obtain 9 mg (38%) of the title compound as off white solid.

$^1$H-NMR (400 MHz, DMSO-$d_6$+$D_2O$) δ ppm: 7.34 (s, 1H), 7.07 (s, 1H), 5.23 (d, 1H, J=7.2 Hz) 4.53 (t, 2H, J=8.4 Hz), 3.42 (brd, 1H, J=12.8 Hz), 3.19 (t, 2H), 2.72-2.66 (m, 1H).

Mass spectrum (ESI): m/z 205.90 (M+H)

(Example 12) Synthesis of 3-(aminomethyl)-6,7-dihydrofuro[2,3-f][2,1]benzoxaborol-1(3H)-ol hydrochloride (Compound 12)

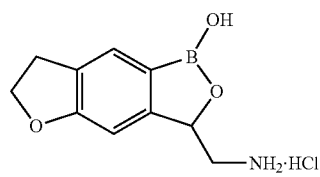

12

The title compound (white solid) was synthesized following the steps described in (Example 11).

Yield: 28 mg (48%).

$^1$H-NMR (400 MHz, DMSO-$d_6$+$D_2O$) δ ppm: 7.59 (s, 1H), 6.90 (s, 1H), 5.23 (br, 1H, J=7.2 Hz), 4.60 (t, 2H, J=10.0 Hz), 3.46 (br, 1H, J=13.6 Hz), 3.20 (t, 2H, J=9.8 Hz), 2.80-2.66 (m, 1H).

Mass spectrum (ESI): m/z 205.92 (M+H), 204.84 (M−H).

Microbiological Assay

A number of different assays can be utilized. In addition to the assay mentioned in hereinafter, one of ordinary skill in the art will know of other assays that can be utilized and can modify an assay for a particular application. Such assays and modification thereon are within the sprit and scope of the present invention.

(Test Example 1) Leucine tRNA Synthetase (LRS) Enzyme Inhibition Assay [IC$_{50}$]

E. coli and P. aeruginosa LRS enzymes were cloned, expressed and purified in-house. The IC$_{50}$ values were determined by using following assay protocol.

Test compounds were diluted in milli-Q water. 5 μL (microliter) of test compound dilution was mixed with 20 μL of reaction mixture consisting of 100 millimolar Tris (Trizma base from Sigma), 120 millimolar potassium chloride (Sigma), 1 molar magnesium chloride (Sigma), 50 millimolar dithiothreitol, 50 mg/mL E. coli tRNA (Roche), 150 micromolar leucine (Sigma), 0.5 microcurie of $^3$H Leucine (Amersham) and 20 μL of appropriate dilution of LRS enzyme, incubate in shaker at about 30° C. for 20 minutes. The reaction was started by adding 5 μL of 40 millimolar ATP (Sigma) and incubated on shaker at the same temperature further for 20 minutes. The reaction was quenched with 150 μL ice cold trichloroacetic acid (10%). The content of each well was transferred to 96 well GF/C plates (from Pall), and washed with 150 μL of trichloroacetic acid (5%) using vacuum manifold (from Pall). Plates were dried and read using Microbeta Wallac liquid scintillation counters after adding 100 μL of scintillation cocktail (Perkin Elmer's OptiPhase 'SuperMix') to each well. IC$_{50}$ was calculated with respect to enzyme control after subtracting background (No enzyme control) using Graph Pad Prism software.

The compound of formula (I) was found to be potent inhibitor of LRS having IC$_{50}$ less than 5 μg/mL for E. coli and less than 10 μg/mL for P. aeruginosa enzymes, respectively as shown in below table.

| Compound No. | IC$_{50}$ (μM) | |
| --- | --- | --- |
| | E. coli LRS | P. aeruginosa LRS |
| 1 | 1.40 | >10 |
| 2 | 3.35 | >10 |
| 3 | 2.50 | 2.20 |
| 4 | 4.50 | 9.50 |
| 5 | 0.80 | 2.30 |
| 6 | <0.12 | <0.12 |
| 7 | 0.80 | 0.60 |
| 8 | 2.10 | 3.20 |
| 9 | 1.70 | 2.70 |
| 10 | 0.38 | 0.62 |
| 11 | 2.90 | >10 |
| 12 | 2.80 | >10 |

(Test Example 2) Method of Testing Susceptibility of Bacterial [MICs]

Minimum inhibitory concentration (MIC) were determined as recommended by the Clinical and Laboratory Standards Institute (CLSI) in 2010 (M100-520), in 2011 (M100-521), 2012 (M100-522) and in 2013 (M100-523) with minor modifications.

In short, bacterial cultures were streaked on Muller Hinton Agar plates and incubated at 35±2° C. for about 18 to 20 hours. Following day colony suspension was prepared in saline and adjusted to 0.5 McFarland using Densitometer. This culture was further diluted 100 fold in Muller Hinton Broth or M9 minimal media or pooled human urine and used for MIC determination. The test compounds were prepared in dimthylesulfoxide (DMSO) at concentration of 1 mg/mL, and diluted to 32 µg/mL in respective media. Further two fold serial dilution were prepared in 96 well microtiter plates. 50 µL of diluted cultures were added to all wells and incubated at 35±2° C. for about 16 to 20 hours.

MICs were determined as lowest concentration of drug that completely inhibits growth of the organism in the microdilution wells as detected by unaided eye.

The compound of formula (I) had MIC less than or equal to 8 µg/mL, or even less than 4 µg/mL for *E. coli* and *K. pneumonia* as shown in below table. The compound of formula (I) also has MIC against *P. aeruginosa*, for example compounds 5, 6, 8, 9 and 10 have MICs of 8, 2, 4, 2 and 1 µg/mL, respectively.

| Compound No. | E. coli ATCC 25922 | K. pneumoniae ATCC 13883 |
|---|---|---|
| 1 | 4 | 4 |
| 2 | 4 | 8 |
| 3 | 1 | 1 |
| 4 | 8 | 16 |
| 5 | 1 | 1 |
| 6 | 1 | 1 |
| 7 | 8 | 16 |
| 8 | 4 | 4 |
| 9 | 2 | 2 |
| 10 | 2 | 0.5 |
| 11 | 4 | 4 |
| 12 | 8 | 16 |

(Test Example 3) Methods of Testing Therapeutic Effects (Test Example 3a) In Vivo Efficacy in Urinary Tract Infection (UTI) Model Mouse *P. aeruginosa* UTI ascending model was used. All animals were infected with *P. aeruginosa* PAO1 by intra-urethral route. Randomization was done 18 hours post infection before starting treatment. Therapy was initiated 18 hours post infection. Animals were treated with 30 mg/kg and 60 mg/kg body weight of test compounds twice daily for 3 days. Animals were sacrificed and cfu loads in kidney and bladder were detected by serial dilution platting on drug free TSA plates on day 4.

Compound 10 showed 4.18 and 3.83 log reduction from the untreated control at the 4$^{th}$ day of infection, at a dose of 60 mg/kg body weight in the kidney and bladder counts respectively.

(Test Example 3b) In Vivo Efficacy in *E. coli* Murine Neutropenic Thigh Infection Model Efficacy of test compounds were evaluated by subcutaneous (SC) route against *E. coli* GK00432 in neutropenic mouse thigh infection model. Study was performed in Swiss albino mice of either sex weighing 20±2 g. Neutropenia was induced by intraperitoneal injections of cyclophosphamide given twice prior to infection (150 mg/kg, at 4 days prior to infection, and 100 mg/kg, at 1 day prior to infection). *E. coli* inoculum (0.1 mL) was injected intra-muscularly in the thigh muscle. After 2 hours, test compound at a dose of 30 mg/kg and 60 mg/kg body weight were administered by subcutaneous route and one group of mice (n=5) was sacrificed to evaluate total live bacterial count per thigh as baseline bacterial loads. Remaining three doses of test compound were administered by subcutaneous route after 2, 4, 8 and 14 hours of the infection. Animals were euthanized, thigh muscles were removed aseptically and homogenized in phosphate buffered saline (3 mL) and serial dilutions plated Tryptone Soya Agar plates 26 hours post infection.

Compound 5 showed 3.8 and 3.1 log reduction in colony forming units (cfu) at the doses 60 mg/kg and 30 mg/kg four times daily (QID) from 26 hours untreated control.

(Test Example 3c) In Vivo Efficacy in *P. aeruginosa* PAO1 Murine Lung Infection Model Overnight grown culture of *P. aeruginosa* PAO-1 on TSA agar was inoculated in Brain heart infusion broth (BHI, DIFCO) and grown in a shaker incubator with shaking at 110 rpm at 35±2° C. overnight. The culture was subcultured in 50 mL of BHI and incubated again at 110 rpm at 35±2° C. on a shaker incubator till the optical density of the culture reaches 0.5-0.7 units. For infection, animals were weighed, randomized and anesthetized by giving isofluorane. Under anesthesia the animals were infected with 50 µL of the inoculum prepared as above by intranasal route. The test compounds were administered at 75 mg/kg body weight by subcutaneous route after 1 hour and 6 hours post infection. Animals were euthanized, lungs were removed aseptically and homogenized in PBS (3 mL) and serial dilutions plated on TSA plates 24 hours post infection.

Compound 6 and 10 showed 4.04 and 3.53 log reduction in cfu at subcutaneous dose of 75 mg/kg twice daily from 24 hours untreated control and 2.58 and 2.07 log reduction in cfu's from baseline (Test Example 4) MICs in Human Urine Against *E. coli* and *K. pneumonia*

Human urine supports bacterial growth and allows spreading of infection from urethra to bladder hence activity in urine is most important. Many antibacterial compounds like fluroquinolones loose activity in human urine at acidic pH (acidic urine promotes rigorous bacterial growth). MICs were performed using CLSI guidelines (2011) against *E. coli* 25922 in Muller Hinton Broth (MHB) and pooled human urine.

The compound of formula (I) did not show significant shift in MIC in human urine compared to Muller Hinton Broth, for instance compounds shown in below table showed less than and equal to two fold shift in MIC.

| | E. coli ATCC 25922 MIC (µg/mL) | |
|---|---|---|
| Compound No. | MHB | Urine pH 5.5 |
| 5 | 2 | 4 |
| 8 | 8 | 16 |
| 9 | 8 | 8 |
| 10 | 2 | 4 |

(Test Example 5) MICs Against *Pseudomonas* Efflux Pump Mutants

Multidrug-resistant (MDR) *P. aeruginosa* isolated from nosocomial infections in intensive care units (ICUs) are often related to altered regulation of the specific efflux pumps and porins in *P. aeruginosa* strains. Tested compounds that show similar activity against efflux pump overproducers and lab strains can be predictive of activity in nosocomial patients infected with MDR strains. To identify such compounds we have determined MICs against *P. aeruginosa* PAO1 against Efflux deleted and overproducer strains.

The compound of formula (I) did not show significant shift in MIC against efflux mutants of *Pseudomonas*, for instance compounds shown in below table showed less than and equal to two fold shift in MIC.

| Compound No. | MIC (µg/mL) *P. aeruginosa* PAO1 | | |
|---|---|---|---|
| | Parent | MexAB del | MexAB over expression |
| 5 | 4 | 4 | 8 |
| 8 | 2 | 4 | 4 |
| 9 | 2 | 2 | 4 |
| 10 | 1 | 1 | 1 |

(Test Example 6) In Vivo Model for Determining Resistance on Therapy

Mouse *P. aeruginosa* UTI ascending model was used. All animals were infected with *P. aeruginosa* PAO1 by intraurethral route. Randomization was done 18 hours post infection before starting treatment. Therapy was initiated 18 hours post infection. Animals were treated with 30 mg/kg and 60 mg/kg body weight of test compounds twice daily for 3 days. Animals were sacrificed and cfu loads in kidney and bladder were detected by serial dilution platting on drug free and drug containing TSA plates on day 4.

(Test Example 7) Frequency of Resistance (FOR) in Presence of Norvaline

The FOR was performed in the presence of sub-MIC concentration of norvaline to evaluate effect on resistance development in M9 minimal agar medium. The FOR was determined by platting approximately $10^{9-10}$ CFU of bacterial culture on drug containing M9 agar plates with 4 to 8 times MIC concentrations of test compounds and fixed concentration of norvaline. Simultaneously serial dilutions of culture were also plated on drug free agar plates to determine total cfu's. Plates were incubated for 48 hours and resulting cfu's were counted. FOR was calculated as cfu's on drug containing plates/cfu's on drug free plates.

The FOR was reduced more than 150 folds in presence of sub MIC concentrations of norvaline when combined with a compound of formula (I) wherein both X represent oxygen atoms.

(Test Example 8) Method for Testing Oral Bioavailability (BA) in Rats and Mouse (Test Example 8a) Oral Bioavailability (BA) in Rats To Male Sprague Dawley Rats (215±10 g) test compound was administered as 2.0 mg/mL solution in milli-Q water (pH 5.0) by intravenous and oral route. The final dose was 4.25 mg/kg body weight (intravenous) or 8.5 mg/kg body weight (oral). Plasma samples analyzed for test compound using LC-MS/MS method. Estimation of pharmacokinetic parameters was done by using moment analysis. WinNonlin software 6.1 (Pharsight) was utilized for the estimation of PK parameters and oral bioavailability. The compound 6 had 72% oral absolute bioavailability in Sprague Dawley Rats.

(Test Example 8b) Oral Bioavailability (BA) in Mouse

To Female Swiss mouse (23±3 g) test compound was administered as 0.5 mg/mL intravenous and 1 mg/mL oral solution in milli-Q water (pH 5.0). The final dose was 4.25 mg/kg body weight (intravenous) and 8.5 mg/kg body weight (oral route). Plasma samples analyzed for test compound using LC-MS/MS method. Estimation of pharmacokinetic parameters was done by using moment analysis. WinNonlin software 6.1 (Pharsight) was utilized for the estimation of PK parameters and oral bioavailability. The compound 6 had 62% oral absolute bioavailability in Swiss mice.

The invention claimed is:

1. A compound represented by general formula (I), a stereoisomer, or a pharmaceutically acceptable salt thereof:

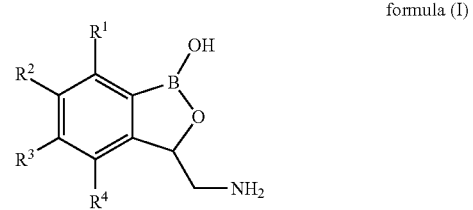

formula (I)

wherein, the adjacent two of $R^1$, $R^2$, $R^3$ and $R^4$ taken together with benzoxaborole structural moeity form tricyclic structure represented by the following formulae:

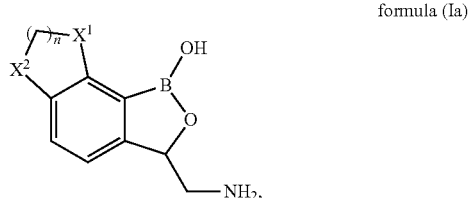

formula (Ia)

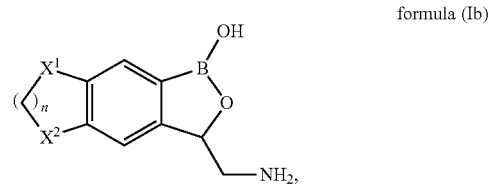

formula (Ib)

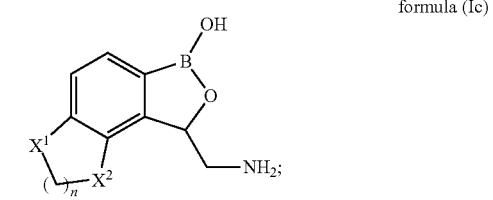

formula (Ic)

while the rest of the two of $R^1$, $R^2$, $R^3$ and $R^4$ which do not percipitate in tricyclic structure formation represent hydrogen atom, X¹ and X², each independently represents a methylene group or oxygen atom and n represents integer of 1 or 2.

2. The compound or a pharmaceutically acceptable salt thereof according to claim 1, wherein the compound of the general formula (I) has the following structure:

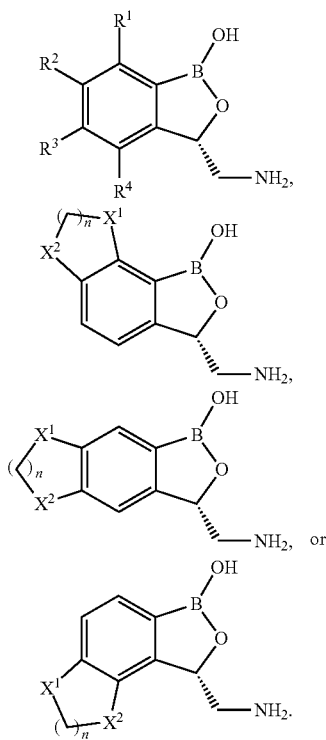

3. The compound, a stereoisomer, or a pharmaceutically acceptable salt thereof according to claim 1, wherein X¹ and X² represent oxygen atoms and n represents 1 or 2.

4. The compound, a stereoisomer, or a pharmaceutically acceptable salt thereof according to claim 1, wherein one of X¹ and X² represents oxygen and the other represents a methylene group, and n represents 1 or 2.

5. The compound, a stereoisomer, or a pharmaceutically acceptable salt thereof according to claim 1, wherein X¹ and X² represent methylene group and n represents 1 or 2.

6. The compound, a stereoisomer, or a pharmaceutically acceptable salt thereof according to claim 1, wherein the compound is selected from the group consisting of:
- 3-(Aminomethyl)[1,3]dioxolo[4,5-f][2,1] benzoxaborol-1(3H)-ol hydrochloride,
- 3-(Aminomethyl)-6,7-dihydro[1,2]oxaborolo[3,4-g][1,4] benzodioxin-1(3H)-ol hydrochloride,
- 3-(Aminomethyl)-3,6,7,8-tetrahydro-1H-indeno[4,5-c][1,2]oxaborol-1-ol hydrochloride,
- 3-(Aminomethyl)-6,7,8,9-tetrahydronaphtho[1,2-c][1,2]oxaborol-1(3H)-ol hydrochloride,
- 8-(Aminomethyl)[1,3]dioxolo[4,5-e][2,1]benzoxaborol-6(8H)-ol hydrochloride,
- (8S)-8-(Aminomethyl)[1,3]dioxolo[4,5-e][2,1]benzoxaborol-6(8H)-ol hydrochloride,
- 9-(Aminomethyl)-2,3-dihydro[1,2]oxaborolo[4,3-f][1,4]benzodioxin-7(9H)-ol hydrochloride,
- 3-(Aminomethyl)-7,8-dihydro[1,2]oxaborolo[3,4-f][1,4]benzodioxin-1(3H)-ol hydrochloride,
- 3-(Aminomethyl) [1,3]dioxolo[4,5-g][2,1]benzoxaborol-1(3H)-ol hydrochloride,
- (3S)-3-(Aminomethyl)[1,3]dioxolo[4,5-g][2,1]benzoxaborol-1(3H)-ol hydrochloride,
- 3-(Aminomethyl)-5,6-dihydrofuro[3,2-f][2,1]benzoxaborol-1(3H)-ol hydrochloride, and
- 3-(Aminomethyl)-6,7-dihydrofuro[2,3-f][2,1]benzoxaborol-1(3H)-ol hydrochloride.

7. The compound or a pharmaceutically acceptable salt thereof according to claim 1, wherein the compound is
- (8S)-8-(Aminomethyl)[1,3]dioxolo[4,5-e][2,1]benzoxaborol-6(8H)-ol hydrochloride, or
- (3S)-3-(Aminomethyl) [1,3]dioxolo[4,5-g][2,1]benzoxaborol-1(3H)-ol hydrochloride.

8. A pharmaceutical composition comprising a therapeutically effective amount of a compound, a stereoisomer, or a pharmaceutically acceptable salt thereof according to claim 1, as its active ingredient.

* * * * *